US007238684B2

(12) United States Patent
Starke et al.

(10) Patent No.: US 7,238,684 B2
(45) Date of Patent: *Jul. 3, 2007

(54) BENZOTHIADIAZEPINE DERIVATIVES, PROCESSES FOR THEIR PREPARATION AND PHARMACEUTICAL COMPOSITIONS CONTAINING THEM

(75) Inventors: Ingemar Starke, Mölndäl (SE); Mikael Ulf Johan Dahlstrom, Mölndäl (SE); Mats Peter Nordberg, Mölndäl (SE); Suzanne Alenfalk, Mölndäl (SE); Andreas Christer Wallberg, Mölndäl (SE); Stig Jonas Bostrom, Mölndäl (SE)

(73) Assignee: AstraZeneca AB, Sodertalje (SE)

( * ) Notice: Subject to any disclaimer, the term of this patent is extended or adjusted under 35 U.S.C. 154(b) by 105 days.

This patent is subject to a terminal disclaimer.

(21) Appl. No.: 10/511,984

(22) PCT Filed: Apr. 23, 2003

(86) PCT No.: PCT/GB03/01742

§ 371 (c)(1),
(2), (4) Date: Oct. 21, 2004

(87) PCT Pub. No.: WO03/091232

PCT Pub. Date: Nov. 6, 2003

(65) Prior Publication Data

US 2005/0143368 A1    Jun. 30, 2005

(30) Foreign Application Priority Data

Apr. 25, 2002 (GB) .............................. 0209467.0

(51) Int. Cl.
C07D 285/36  (2006.01)
A61K 31/554  (2006.01)

(52) U.S. Cl. .................. 514/211.08; 540/545
(58) Field of Classification Search ................ 540/545; 514/211.08
See application file for complete search history.

(56) References Cited

U.S. PATENT DOCUMENTS

| 6,277,831 | B1 | 8/2001 | Frick et al. |
| 6,387,944 | B1 | 5/2002 | Frick et al. |
| 6,906,058 | B2 | 6/2005 | Starke et al. |
| 7,125,864 | B2 | 10/2006 | Starke et al. |
| 7,132,416 | B2 | 11/2006 | Starke et al. |
| 2002/0142054 | A1 | 10/2002 | Marlett et al. |
| 2005/0113362 | A1 | 5/2005 | Lindstedt et al. |
| 2005/0171204 | A1 | 8/2005 | Lindstedt et al. |
| 2005/0282822 | A1 | 12/2005 | Alstermark et al. |

FOREIGN PATENT DOCUMENTS

| DE | 19825804 | 12/1999 |
| EP | 0372542 | 6/1990 |
| EP | 0 864 582 A | 9/1998 |
| GB | 2262888 | 7/1993 |
| WO | WO 93/16055 | 8/1993 |
| WO | WO 94/18183 | 8/1994 |
| WO | WO 94/18184 | 8/1994 |
| WO | WO 96/05188 | 2/1996 |
| WO | WO 96/08484 | 3/1996 |
| WO | WO 96/16051 | 5/1996 |
| WO | WO 97/33882 | 9/1997 |
| WO | 98/38182 A | 9/1998 |
| WO | WO 98/40375 | 9/1998 |
| WO | WO 99/01149 | 1/1999 |
| WO | WO 99/32478 | 7/1999 |
| WO | WO 99/35135 | 7/1999 |
| WO | WO 99/64409 | 12/1999 |
| WO | WO 99/64410 | 12/1999 |
| WO | WO 00/01687 | 1/2000 |
| WO | WO 00/38725 | 7/2000 |
| WO | WO 00/38726 | 7/2000 |
| WO | WO 00/38727 | 7/2000 |
| WO | WO 00/38728 | 7/2000 |
| WO | WO 00/38729 | 7/2000 |
| WO | WO 00/47568 | 8/2000 |
| WO | WO 00/61568 | 10/2000 |
| WO | WO 00/62810 | 10/2000 |
| WO | WO 01/60807 | 8/2001 |
| WO | 01/66533 A | 9/2001 |
| WO | WO 01/66533 | 9/2001 |
| WO | WO 01/68096 | 9/2001 |
| WO | WO 01/68637 | 9/2001 |
| WO | WO 02/08211 | 1/2002 |
| WO | WO 02/32428 | 4/2002 |
| WO | 02/50051 A | 6/2002 |
| WO | WO 02/50051 | 6/2002 |
| WO | WO 02/053548 | 7/2002 |
| WO | 03/022286 A | 3/2003 |
| WO | WO 03/020710 | 3/2003 |
| WO | WO 03/022286 | 3/2003 |
| WO | WO 03/022825 | 3/2003 |

(Continued)

OTHER PUBLICATIONS

Govers et al., (1994) "Characterization of the adsorption of conjugated and unconjugated bile acids to insoluble, amorphous calcium phosphate" Journal of Lipid Research, 35(5): 741-748.

(Continued)

Primary Examiner—Bruck Kifle
(74) Attorney, Agent, or Firm—Morgan Lewis & Bockius LLP

(57) ABSTRACT

The present invention relates to compounds of formula (I): wherein $R^v$, $R^1$, $R^2$, $R^x$, $R^y$, $R^3$, $R^4$, $R^5$, $R^6$, $R^z$ and v are as defined within; pharmaceutically acceptable salts, solvates, solvates or such salts and prodrugs thereof and their use as ileal bile acid transport (IBAT) inhibitors for the treatment of hyperlipidaemia. Processes for their manufacture and pharmaceutical compositions containing them are also described.

12 Claims, No Drawings

FOREIGN PATENT DOCUMENTS

| | | |
|---|---|---|
| WO | WO 03/022830 | 3/2003 |
| WO | WO 03/051821 | 6/2003 |
| WO | WO 03/051822 | 6/2003 |
| WO | WO 03/061663 | 7/2003 |
| WO | WO 03/106482 | 12/2003 |
| WO | WO 2004/006899 | 1/2004 |
| WO | WO 2004/076430 | 9/2004 |
| WO | WO 2004/089350 | 10/2004 |

OTHER PUBLICATIONS

Higaki et al., (1998) "Inhibition of Ileal $Na^+$/Bile Acid Cotransporter by S-8921 Reduces Serum Cholesterol and Prevents Atherosclerosis in Rabbits" Ateriosclerosis, Thrombosis, and Vascular Biology 18(8): 1304-1311.

Ishibashi et al., (1993) "Hypercholesterolemia in low density lipoprotein receptor knockout mice and its reversal by adenovirus-mediated gene delivery" Journal of Clinical Investigation 92(2): 883-893.

Lewis et al., (1995) "Effects of 2164U90 on ileal bile acid absorption and serum cholesterol in rats and mice" Journal of Lipid Research, 36(5): 1098-1105.

Plump et al., (1992) "Severe hypercholesterolemia and atherosclerosis in apolipoprotein E-deficient mice created by homologous recombination in ES cells" Cell 71(2):343-353.

Schiller (2001) "The therapy of constipation" Alimentary Pharmacology and Therapeutics 15(6): 749-763.

Sprong et al., (2002) "Dietary Calcium Phosphate Promotes Listeria monocytogenes Colonization and Translocation in Rats Fed Diets Containing Corn Oil but Not Milk Fat" J. Nutrition (US) 132(6): 1269-1274.

Van Tilburg et al., (1989) "Na+-dependent bile acid transport in the ileum: The balance between diarrhea and constipation" Gastroenterology 98(1): 25-32.

Welberg et al., (1991) "Calcium and the prevention of colon cancer" Scandinavian J. Gastroenterology Suppl Norway 188: 52-59.

BENZOTHIADIAZEPINE DERIVATIVES, PROCESSES FOR THEIR PREPARATION AND PHARMACEUTICAL COMPOSITIONS CONTAINING THEM

This application is a Section 371 US National Stage application of PCT/GB03/01742, filed Apr. 23, 2003.

This invention relates to benzothiadiazepine derivatives, or pharmaceutically acceptable salts, solvates, solvates of such salts and prodrugs thereof. These benzothiadiazepines possess ileal bile acid transport (IBAT) inhibitory activity and accordingly have value in the treatment of disease states associated with hyperlipidaemic conditions and they are useful in methods of treatment of a warm-blooded animal, such as man. The invention also relates to processes for the manufacture of said benzothiadiazepine derivatives, to pharmaceutical compositions containing them and to their use in the manufacture of medicaments to inhibit IBAT in a warm-blooded animal, such as man.

It is well-known that hyperlipidaemic conditions associated with elevated concentrations of total cholesterol and low-density lipoprotein cholesterol are major risk factors for cardiovascular atherosclerotic disease (for instance "Coronary Heart Disease: Reducing the Risk; a Worldwide View" Assman G., Carmena R. Cullen P. et al; Circulation 1999, 100, 1930–1938 and "Diabetes and Cardiovascular Disease: A Statement for Healthcare Professionals from the American Heart Association" Grundy S, Benjamin L., Burke G., et al; Circulation, 1999, 100, 1134–46). Interfering with the circulation of bile acids within the lumen of the intestinal tracts is found to reduce the level of cholesterol. Previous established therapies to reduce the concentration of cholesterol involve, for instance, treatment with HMG-CoA reductase inhibitors, preferably statins such as simvastatin and fluvastatin, or treatment with bile acid binders, such as resins. Frequently used bile acid binders are for instance cholestyramine and cholestipol. One recently proposed therapy ("Bile Acids and Lipoprotein Metabolism: a Renaissance for Bile Acids in the Post Statin Era" Angelin B, Eriksson M, Rudling M; Current Opinion on Lipidology, 1999, 10, 269–74) involved the treatment with substances with an IBAT inhibitory effect.

Re-absorption of bile acid from the gastro-intestinal tract is a normal physiological process which mainly takes place in the ileum by the IBAT mechanism. Inhibitors of IBAT can be used in the treatment of hypercholesterolaemia (see for instance "Interaction of bile acids and cholesterol with nonsystemic agents having hypocholesterolaemic properties", Biochemica et Biophysica Acta, 1210 (1994) 255–287). Thus, suitable compounds having such inhibitory IBAT activity are also useful in the treatment of hyperlipidaemic conditions. Compounds possessing such IBAT inhibitory activity have been described, see for instance the compounds described in WO 93/16055, WO 94/18183, WO 94/18184, WO 96/05188, WO 96/08484, WO 96/16051, WO 97/33882, WO 98/38182, WO 99/35135, WO 98/40375, WO 99/35153, WO 99/64409, WO 99/64410, WO 00/01687, WO 00/47568, WO 00/61568, WO 01/68906, DE 19825804, WO 00/38725, WO 00/38726, WO 00/38727, WO 00/38728, WO 00/38729, WO 01/68906 and EP 0 864 582.

A further aspect of this invention relates to the use of the compounds of the invention in the treatment of dyslipidemic conditions and disorders such as hyperlipidaemia, hypertrigliceridemia, hyperbetalipoproteinemia (high LDL), hyperprebetalipoproteinemia (high VLDL), hyperchylomicronemia, hypolipoproteinemia, hypercholesterolemia, hyperlipoproteinemia and hypoalphalipoproteinemia (low HDL). In addition, these compounds are expected to be useful for the prevention and treatment of different clinical conditions such as atherosclerosis, arteriosclerosis, arrhythmia, hyper-thrombotic conditions, vascular dysfunction, endothelial dysfunction, heart failure, coronary heart diseases, cardiovascular diseases, myocardial infarction, angina pectoris, peripheral vascular diseases, inflammation of cardiovascular tissues such as heart, valves, vasculature, arteries and veins, aneurisms, stenosis, restenosis, vascular plaques, vascular fatty streaks, leukocytes, monocytes and/or macrophage infiltration, intimal thickening, medial thinning, infectious and surgical trauma and vascular thrombosis, stroke and transient ischaemic attacks.

The present invention is based on the discovery that certain benzothiadiazepine compounds surprisingly inhibit IBAT. Such properties are expected to be of value in the treatment of disease states associated with hyperlipidaemic conditions.

Accordingly, the present invention provides a compound of formula (I):

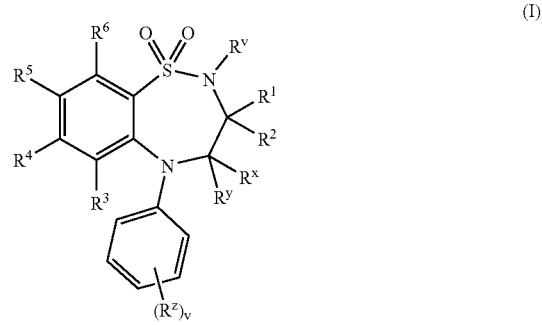

(I)

wherein:

$R^v$ is selected from hydrogen or $C_{1-6}$alkyl;

One of $R^1$ and $R^2$ are selected from hydrogen or $C_{1-6}$alkyl and the other is selected from $C_{1-6}$alkyl;

$R^x$ and $R^y$ are independently selected from hydrogen, hydroxy, amino, mercapto, $C_{1-6}$alkyl, $C_{1-6}$-alkoxy, N—($C_{1-6}$-alkyl)amino, N,N—($C_{1-6}$alkly)$_2$amino, $C_{1-6}$alkylS(O)$_a$ wherein a is 0 to 2;

$R^2$ is selected from halo, nitro, cyano, hydroxy, amino, carboxy, carbamoyl, mercapto, sulphamoyl, $C_{1-6}$alkyl, $C_{2-6}$alkynyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$-alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl and N,N—($C_{1-6}$alkyl$_2$ sulphamoyl;

v is 0–5;

one of $R^4$ and $R^5$ is a group of formula (IA):

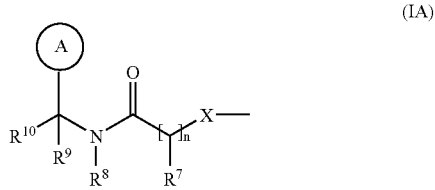

(IA)

$R^3$ and $R^6$ and the other of $R^4$ and $R^5$ are independently selected from hydrogen, halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkly)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-4}$alkyl)sulphamoyl and N,N—($C_{1-6}$alkyl)sulphamoyl; wherein $R^3$ and $R^6$ and the other of $R^4$ and $R^5$ may be optionally substituted on carbon by one or more $R^{17}$;

X is —O—, —N($R^a$)—, —S(O)$_b$— or —CH($R^a$)—; wherein $R^1$ is hydrogen or $C_{1-6}$alkyl and b is 0–2;

Ring A is aryl or heteroaryl; wherein Ring A is optionally substituted on carbon by one or more substituents selected from $R^{18}$;

$R^7$ is hydrogen, $C_{1-6}$alkyl, carbocyclyl or heterocyclyl; wherein $R^7$ is optionally substituted on carbon by one or more substituents selected from $R^{19}$; and wherein if said heterocyclyl contains an —NH— group, that nitrogen may be optionally substituted by a group selected from $R^{20}$;

$R^8$ is hydrogen or $C_{1-6}$alkyl;

$R^9$ is hydrogen or $C_{1-6}$-alkyl;

$R^{10}$ is hydrogen, halo, nitro, cyano, hydroxy, amino, carbamoyl, mercapto, sulphamoyl, hydroxyaminocarbonyl, $C_{1-10}$alkyl, $C_{2-10}$alkenyl, $C_{2-10}$alkynyl, $C_{1-10}$alkoxy, $C_{1-10}$alkanoyl, $C_{1-10}$alkanoyloxy, N—($C_{1-10}$alkyl)amino, N,N—($C_{1-10}$alkyl)$_2$amino, N,N,N—($C_{1-10}$alkyl)$_3$ammonio, $C_{1-10}$alkanoylamino, N—($C_{1-10}$alkyl)carbamoyl, N,N—($C_{1-10}$alkyl)$_2$carbamoyl, $C_{1-10}$alkylS(O)$_a$ wherein a is 0 to 2, N—($C_{1-10}$alkyl)sulphamoyl, N,N—($C_{1-10}$alkyl)$_2$sulphamoyl, N—($C_{1-10}$alkyl)sulphamoylamino, N,N—($C_{1-10}$alkyl)$_2$sulphamoylamino, $C_{1-10}$alkoxycarbonylamino, carbocyclyl, carbocyclyl$C_{1-10}$alkyl, heterocyclyl, heterocyclyl$C_{1-10}$alkyl, carbocyclyl-($C_{1-10}$alkylene)$_p$-$R^{21}$-($C_{1-10}$alkylene)$_q$- or heterocyclyl-($C_{1-10}$alkylene)$_r$-$R^{22}$—($C_{1-10}$alkylene)$_s$-; wherein $R^{10}$ is optionally substituted on carbon by one or more substituents selected from $R^{23}$; and wherein if said heterocyclyl contains an —NH— group, that nitrogen maybe optionally substituted by a group selected from $R^{24}$; or $R^{10}$ is a group of formula IB):

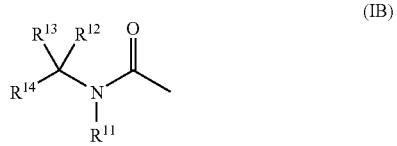

(IB)

wherein:

$R^{11}$ is hydrogen or $C_{1-6}$alkyl;

$R^{12}$ and $R^{13}$ are independently selected from hydrogen, halo, carbamoyl sulphamoyl $C_{1-10}$alkyl, $C_{2-10}$alkenyl, $C_{2-10}$alkynyl, $C_{1-10}$alkanoyl, N—($C_{1-10}$alkyl)carbamoyl, N,N—($C_{1-10}$alkyl)$_2$carbamoyl, $C_{1-10}$alkylS(O)$_a$ wherein a is 0 to 2, N—($C_{1-10}$alkyl)sulphamoyl, N,N—($C_{1-10}$alkyl)$_2$sulphamoyl, N—($C_{1-10}$alkyl)sulphamoylamino, N,N—($C_{1-10}$alkyl)$_2$sulphamoylamino, carbocyclyl or heterocyclyl; wherein $R^{12}$ and $R^{13}$ may be independently optionally substituted on carbon by one or more substituents selected from $R^{25}$; and wherein if said heterocyclyl contains an —NH— group, that nitrogen maybe optionally substituted by a group selected from $R^{26}$;

$R^{14}$ is selected from hydrogen, halo, carbamoyl, sulphamoyl, hydroxyaminocarbonyl, $C_{1-10}$alkyl, $C_{2-10}$alkenyl, $C_{2-10}$alkanoyl, $C_{1-10}$alkanoyl, N—($C_{1-10}$alkyl)carbamoyl, N,N—($C_{1-10}$alkyl)$_2$carbamoyl, $C_{1-10}$alkylS(O)$_a$ wherein a is 0 to 2, N—($C_{1-10}$alkyl)sulphamoyl, N,N—($C_{1-10}$alkyl)$_2$sulphamoyl, N—($C_{1-10}$alkyl)sulphamoylamino, N,N—($C_{1-10}$alkyl)$_2$sulphamoylamino, carbocyclyl, carbocyclyl$C_{1-10}$alkyl, heterocyclyl, heterocyclyl$C_{1-10}$alkyl, carbocyclyl-($C_{1-10}$alkylene)$_p$-$R^{27}$—($C_{1-10}$alkylene)$_q$- or heterocyclyl-($C_{1-10}$alkylene)$_r$-$R^{28}$—($C_{1-10}$alkylene)$_s$-; wherein $R^{14}$ may be optionally substituted on carbon by one or more substituents selected from $R^{29}$; and wherein if said heterocyclyl contains an —NH— group, that nitrogen may be optionally substituted by a group selected from $R^{30}$; or $R^{14}$ is a group of formula (IC):

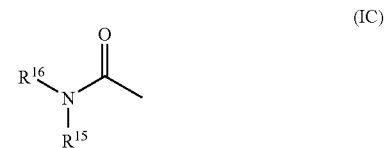

(IC)

$R^{15}$ is hydrogen or $C_{1-6}$alkyl; and $R^{16}$ is hydrogen or $C_{1-6}$alkyl; wherein $R^{16}$ may be optionally substituted on carbon by one or more groups selected from $R^{31}$; or $R^{15}$ and $R^{16}$ together with the nitrogen to which they are attached form a heterocyclyl; wherein said heterocyclyl may be optionally substituted on carbon by one or more $R^{37}$; and wherein if said heterocyclyl contains an —NH— group, that nitrogen may be optionally substituted by a group selected from $R^{38}$;

n is 1–3; wherein the values of $R^7$ may be the same or different;

$R^{17}$, $R^{18}$, $R^{19}$, $R^{23}$, $R^{25}$, $R^{29}$, $R^{31}$ and $R^{37}$ are independently selected from halo, nitro, cyano, hydroxy, amino, carbamoyl, mercapto, sulphamoyl, hydroxyaminocarbonyl, $C_{1-10}$alkyl, $C_{2-10}$alkenyl, $C_{2-10}$alkynyl, $C_{1-10}$alkoxy, $C_{1-10}$alkanoyl, $C_{1-10}$alkanoyloxy, N—($C_{1-10}$alkyl)amino, N,N—($C_{1-10}$alkyl)$_2$amino, N,N,N—($C_{1-10}$alkyl)$_3$ammonio, $C_{1-10}$alkanoylamino, N—($C_{1-10}$alkyl)carbamoyl, N,N—($C_{1-10}$alkyl)$_2$carbamoyl, $C_{1-10}$alkylS(O)$_a$ wherein a is 0 to 2, N—($C_{1-10}$alkyl)sulphamoyl, N,N—($C_{1-10}$alkyl)$_2$sulphamoyl, N—($C_{1-10}$alkyl)sulphamoylamino, N,N—($C_{1-10}$alkyl)$_2$sulphamoylamino, $C_{1-10}$alkoxycarbonylamino, carbocyclyl, carbocyclyl$C_{1-10}$alkyl, heterocyclyl, heterocyclyl$C_{1-10}$alkyl, carbocyclyl-($C_{1-10}$alkylene)$_p$-$R^{32}$—($C_{1-10}$alkylene)$_q$- or heterocyclyl-($C_{1-10}$alkylene)$_r$-$R^{33}$—($C_{1-10}$alkylene)$_s$-; wherein $R^{17}$, $R^{18}$, $R^{19}$, $R^{23}$, $R^{25}$, $R^{29}$, $R^{31}$ and $R^{37}$ may be independently optionally substituted on carbon by one or more $R^{34}$; and wherein if said heterocyclyl contains an —NH— group, that nitrogen may be optionally substituted by a group selected from $R^{35}$;

$R^{21}$, $R^{22}$, $R^{27}$, $R^{28}$, $R^{32}$ or $R^{33}$ are independently selected from —O—, —NR$^{36}$—, —S(O)$_x$—, —NR$^{36}$C(O)NR$^{36}$—, —NR$^{36}$C(S)NR$^{36}$—, —OC(O)N=C—, —NR$^{36}$C(O)— or —C(O)NR$^{36}$—; wherein $R^{36}$ is selected from hydrogen or $C_{1-6}$alkyl, and x is 0–2;

p, q, r and s are independently selected from 0–2;

$R^{34}$ is selected from halo, hydroxy, cyano, carbamoyl, ureido, amino, nitro, carbamoyl, mercapto, sulphamoyl, trifluoromethyl, trifluoromethoxy, methyl, ethyl, methoxy, ethoxy, vinyl, allyl, ethynyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl, N,N-dimethylsulphamoyl, N-methylsulphamoylamino and N,N-dimethylsulphamoylamino;

$R^{20}, R^{24}, R^{26}, R^{30}, R^{35}$ and $R^{38}$ are independently selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkylcarbamoyl, benzyl, benzyloxycarbonyl, benzoyl and phenylsulphonyl; or a pharmaceutically acceptable salt, solvate, solvate of such a salt or a prodrug thereof.

A further aspect of the invention provides a compound of formula (I):

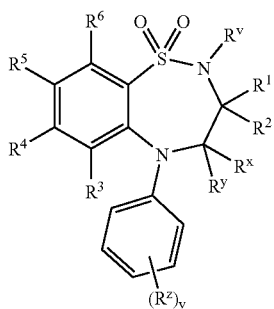

(I)

wherein:

$R^v$ is selected from hydrogen or $C_{1-6}$alkyl;

One of $R^1$ and $R^2$ are selected from hydrogen or $C_{1-6}$alkyl and the other is selected from $C_{1-6}$alkyl;

$R^x$ and $R^y$ are independently selected from hydrogen, hydroxy, amino, mercapto, $C_{1-6}$alkly, $C_{1-6}$alkoxy, N—($C_{1-6}$alkyl)amino, N,N—($C_{1-6}$alkyl)$_2$amino, $C_{1-6}$alkylS(O)$_a$ wherein a is 0 to 2;

$R^z$ is selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl and N,N—($C_{1-6}$alkyl)$_2$sulphamoyl;

v is 0–5;

one of $R^4$ and $R^5$ is a group of formula (IA):

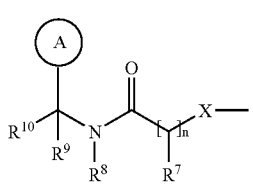

(IA)

$R^3$ and $R^6$ and the other of $R^4$ and $R^5$ are independently selected from hydrogen, halo, nitro, cyano, hydroxy, amino, carboxy, carbamoyl, mercapto, sulphamoyl, $C_{1-6}$alkyl, $C_{2-6}$alkenyl, $C_{2-6}$alkyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl and N,N—($C_{1-6}$alkyl)$_2$sulphamoyl; wherein $R^3$ and $R^6$ and the other of $R^4$ and $R^5$ may be optionally substituted on carbon by one or more $R^{17}$;

X is —O—, —N($R^a$)—, —S(O)$_b$— or —CH($R^a$)—; wherein $R^a$ is hydrogen or $C_{1-6}$alkyl and b is 0–2;

Ring A is aryl or heteroaryl; wherein Ring A is optionally substituted on carbon by one or more substituents selected from $R^{18}$;

$R^7$ is hydrogen, $C_{1-6}$alkyl, carbocyclyl or heterocyclyl; wherein $R^7$ is optionally substituted on carbon by one or more substituents selected from $R^{19}$; and wherein if said heterocyclyl contains an —NH— group, that nitrogen may be optionally substituted by a group selected from $R^{20}$;

$R^8$ is hydrogen or $C_{1-6}$alkyl;

$R^9$ is hydrogen or $C_{1-6}$alkly;

$R^{10}$ is hydrogen, halo, nitro, cyano, hydroxy, amino, carbamoyl, mercapto, sulphamoyl, hydroxyaminocarbonyl, $C_{1-10}$alkyl, $C_{2-10}$alkenyl, $C_{2-10}$alkynyl, $C_{1-10}$alkoxy, $C_{1-10}$alkanoyl, $C_{1-10}$alkanoyloxy, N—($C_{1-10}$alkyl)amino, N,N—($C_{1-10}$alkyl)$_2$amino, N,N,N—($C_{1-10}$alkyl)$_3$ammonio, $C_{1-10}$alkanoylamino, N—($C_{1-10}$alkyl)carbamoyl, N,N—($C_{1-10}$alkyl)$_2$carbamoyl, $C_{1-10}$alkylS(O)$_a$ wherein a is 0 to 2, N—($C_{1-10}$alkyl)sulphamoyl, N,N—($C_{1-10}$alkyl)$_2$sulphamoyl, N—($C_{1-10}$alkyl)sulphamoylamino, N,N—($C_{1-10}$alkyl)$_2$sulphamoylamino, $C_{1-10}$alkoxycarbonylamino, carbocyclyl, carbocyclyl$C_{1-10}$alkyl, heterocyclyl, heterocyclyl$C_{1-10}$alkyl, carbocyclyl-($C_{1-10}$alkylene)$_p$-$R^{21}$—($C_{1-10}$alkylene)$_q$- or heterocyclyl-($C_{1-10}$alkylene)$_r$-$R^{22}$—($C_{1-10}$alkylene)$_s$-; wherein $R^{10}$ is optionally substituted on carbon by one or more substituents selected from $R^{23}$; and wherein if said heterocyclyl contains an —NH— group, that nitrogen may be optionally substituted by a group selected from $R^{24}$; or $R^{10}$ is a group of formula (IB):

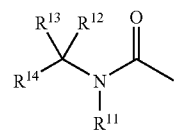

(IB)

wherein:

$R^{11}$ is hydrogen or $C_{1-6}$alkyl;

$R^{12}$ and $R^{13}$ are independently selected from hydrogen, halo, carbamoyl, sulphamoyl, $C_{1-10}$alkyl, $C_{2-10}$alkenyl, $C_{2-10}$alkynyl, $C_{1-10}$alkanoyl, N—($C_{1-10}$alkyl)carbamoyl, N,N—($C_{1-10}$alkyl)$_2$carbamoyl, $C_{1-10}$alkylS(O)$_a$ wherein a is 0 to 2, N—($C_{1-10}$alkyl)sulphamoyl, N,N—($C_{1-10}$alkyl)$_2$sulphamoyl, N—($C_{1-10}$alkyl)sulphamoylamino, N,N—($C_{1-10}$alkyl)$_2$sulphamoylamino, carbocyclyl or heterocyclyl; wherein $R^{12}$ and $R^{13}$ may be independently optionally substituted on carbon by one or more substituents selected from $R^{25}$; and wherein if said heterocyclyl contains an —NH— group, that nitrogen may be optionally substituted by a group selected from $R^{26}$;

$R^{14}$ is selected from hydrogen, halo, carbamoyl, sulphamoyl, hydroxyaminocarbonyl, $C_{1-10}$alkyl, $C_{1-10}$alkenyl, $C_{1-10}$alkynyl, $C_{1-10}$alkanoyl, N—($C_{1-10}$alkyl)carbamoyl, N,N—($C_{1-10}$alkyl)$_2$carbamoyl, $C_{1-10}$alkylS(O)$_a$ wherein a is 0 to 2, N—($C_{1-10}$alkyl)sulphamoyl, N,N—($C_{1-10}$alkyl)$_2$sulphamoyl, N—($C_{1-10}$alkyl)sulphamoylamino, N,N—($C_{1-10}$alkyl)$_2$sulphamoylamino, carbocyclyl, carbocyclyl$C_{1-10}$, heterocyclyl, heterocyclyl$C_{1-10}$alkyl, carbocyclyl-($C_{1-10}$alkylene)$_p$-$R^{27}$—($C_{1-10}$alkylene)$_q$- or heterocyclyl-($C_{1-10}$alkylene)$_r$-$R^{28}$—($C_{1-10}$alkylene)$_s$-; wherein $R^{14}$ may be optionally substituted on carbon by one or more substituents selected from $R^{29}$; and wherein if said heterocyclyl contains an —NH— group, that nitrogen may be optionally substituted by a group selected from $R^{30}$; or $R^{14}$ is a group of formula (IC):

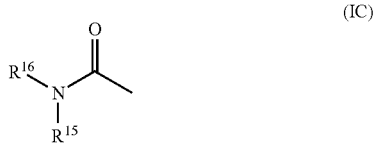

(IC)

$R^{15}$ is hydrogen or $C_{1-6}$alkyl;
$R^{16}$ is hydrogen or $C_{1-6}$alkyl; wherein $R^{16}$ may be optionally substituted on carbon by one or more groups selected from $R^{31}$;
n is 1–3; wherein the values of $R^7$ may be the same or different;
$R^{17}$, $R^{18}$, $R^{19}$, $R^{23}$, $R^{25}$, $R^{29}$ or $R^{31}$ are independently selected from halo, nitro, cyano, hydroxy, amino, carbamoyl, mercapto, sulphamoyl, hydroxyaminocarbonyl $C_{1-10}$alkyl, $C_{2-10}$alkenyl, $C_{2-10}$alkynyl, $C_{1-10}$alkoxy, $C_{1-10}$alkanoyl, $C_{1-10}$alkanoyloxy, N—($C_{1-10}$alkyl)amino, N,N—($C_{1-10}$alkyl)$_2$amino, N,N,N—($C_{1-10}$alkyl)$_3$ammonio, $C_{1-10}$alkanoylamino, N—($C_{1-10}$alkyl)carbamoyl, N,N—($C_{1-10}$alkyl)$_2$carbamoyl, $C_{1-10}$alkylS(O)$_a$ wherein a is 0 to 2, N—($C_{1-10}$alkyl)sulphamoyl, N,N—($C_{1-10}$alkyl)sulphamoyl, N—($C_{1-10}$alkyl)sulphamoylamino, N,N—($C_{1-10}$alkyl)$_2$sulphamoylamino, $C_{1-10}$alkoxycarbonylamino, carbocyclyl carbocyclyl$C_{1-10}$alkly, heterocyclyl, heterocyclyl$C_{1-10}$alkyl, carbocyclyl($C_{1-10}$alkylene)$_p$-$R^{32}$—($C_{1-10}$alkylene)$_q$- or heterocyclyl-($C_{1-10}$alkylene)$_r$-$R^{33}$—($C_{1-10}$alkylene)$_s$-; wherein $R^{17}$, $R^{18}$, $R^{19}$, $R^{23}$, $R^{25}$, $R^{29}$ or $R^{31}$ may be independently optionally substituted on carbon by one or more $R^{34}$; and wherein if said heterocyclyl contains an —NH— group, that nitrogen may be optionally substituted by a group selected from $R^{35}$;
$R^{21}$, $R^{22}$, $R^{27}$, $R^{28}$, $R^{32}$ or $R^{33}$ are independently selected from —O—, —NR$^{36}$—, —S(O)$_x$—, —NR$^{36}$C(O)NR$^{36}$—, —NR$^{36}$C(S)NR$^{36}$—, —OC(O)N=C—, —NR$^{36}$C(O)— or —C(O)NR$^{36}$—; wherein $R^{36}$ is selected from hydrogen or $C_{1-6}$alkyl, and x is 0–2;
p, q, r and s are independently selected from 0–2;
$R^{34}$ is selected from halo, hydroxy, cyano, carbamoyl, ureido, amino, nitro, carbamoyl, mercapto, sulphamoyl, trifluoromethyl, trifluoromethoxy, methyl, ethyl, methoxy, ethoxy, vinyl, allyl, ethynyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl, N,N-dimethylsulphamoyl, N-methylsulphamoylamino and N,N-dimethylsulphamoylamino;
$R^{20}$, $R^{24}$, $R^{26}$, $R^{30}$ or $R^{35}$ are independently selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl; or a pharmaceutically acceptable salt, solvate, solvate of such a salt or a prodrug thereof.

In this specification the term "alkyl" includes both straight and branched chain alkyl groups but references to individual alkyl groups such as "propyl" are specific for the straight chain version only. For example, "$C_{1-6}$alkyl" includes $C_{1-4}$alkyl, $C_{1-3}$alkyl, propyl, isopropyl and t-butyl. However, references to individual alkyl groups such as 'propyl' are specific for the straight chained version only and references to individual branched chain alkyl groups such as 'isopropyl' are specific for the branched chain version only. A similar convention applies to other radicals, for example "phenyl$C_{1-6}$alkyl" would include phenyl$C_{1-6}$alkyl, benzyl, 1-phenylethyl and 2-phenylethyl. The term "halo" refers to fluoro, chloro, bromo and iodo.

Where optional substituents are chosen from "one or more" groups it is to be understood that this definition includes all substituents being chosen from one of the specified groups or the substituents being chosen from two or more of the specified groups.

"Heteroaryl" is a totally unsaturated, mono or bicyclic ring containing 3–12 atoms of which at least one atom, particularly 1–3 atoms, are chosen from nitrogen, sulphur or oxygen, which may, unless otherwise specified, be carbon or nitrogen linked. Preferably "heteroaryl" refers to a totally unsaturated, monocyclic ring containing 5 or 6 atoms or a bicyclic ring containing 9 or 10 atoms of which at least one atom is chosen from nitrogen, sulphur or oxygen, which may, unless otherwise specified, be carbon or nitrogen linked. Examples and suitable values of the term n"heteroaryl" are thienyl, isoxazolyl, imidazolyl, pyrrolyl, thiadiazolyl, isothiazolyl, triazolyl, pyranyl, indolyl, pyrimidyl, pyrazinyl, pyridazinyl, pyridyl and quinolyl. Preferably the term "heteroaryl" refers to thienyl or indolyl. "Heteroaryl" is not tetrazolyl.

"Aryl" is a totally unsaturated, mono or bicyclic carbon ring that contains 3–12 atoms. Preferably "aryl" is a monocyclic ring containing 5 or 6 atoms or a bicyclic ring containing 9 or 10 atoms. Suitable values for "aryl" include phenyl or naphthyl. Particularly "aryl" is phenyl.

A "heterocyclyl" is a saturated, partially saturated or unsaturated, mono or bicyclic ring containing 3–12 atoms of which at least one atom, particularly 1–3 atoms, are chosen from nitrogen, sulphur or oxygen, which may, unless otherwise specified, be carbon or nitrogen linked, wherein a —CH$_2$— group can optionally be replaced by a —C(O)— or a ring sulphur atom may be optionally oxidised to form the S-oxides. Preferably a "heterocyclyl" is a saturated, partially saturated or unsaturated, mono or bicyclic ring containing 5 or 6 atoms of which at least one atom is chosen from nitrogen, sulphur or oxygen, which may, unless otherwise specified, be carbon or nitrogen linked, wherein a —CH$_2$— group can optionally be replaced by a —C(O)— or a ring sulphur atom may be optionally oxidised to form S-oxide(s). Examples and suitable values of the term "heterocyclyl" are thiazolidinyl, pyrrolidinyl, pyrrolinyl, 2-pyrrolidonyl, 2,5-dioxopyrrolidinyl, 2-benzoxazolinonyl, 1,1-dioxotetrahydrothienyl, 2,4-dioxoimidazolidinyl, 2-oxo-1,3,4-(4-triazolinyl), 2-oxazolidinonyl, 5,6 dihydrouracilyl, 1,3-benzodioxolyl, 1,2,4-oxadiazolyl, 2-azabicyclo[2.2.1]heptyl, 4-thiazolidonyl, morpholino, 2-oxotetrahydrofuranyl, tetrahydrofuranyl, 2,3-dihydrobenzofuranyl, benzothienyl, tetrahydropyranyl, piperidyl, 1-oxo-1,3-dihydroisoindolyl, piperazinyl, thiomorpholino, 1,1-dioxothiomorpholino, tetrahydropyranyl, 1,3-dioxolanyl, homopiperazinyl, thienyl, isoxazolyl, imidazolyl, pyrrolyl, thiadiazolyl, isothiazolyl, 1,2,4-triazolyl, 1,3,4-triazolyl, pyranyl, indolyl, pyrimidyl, thiazolyl, pyrazinyl, pyridazinyl, pyridyl, 4-pyridonyl, quinolyl and 1-isoquinolonyl. "Heterocyclyl" is not tetrazolyl.

A "carbocyclyl" is a saturated, partially saturated or unsaturated, mono or bicyclic carbon ring that contains 3–12 atoms; wherein a —CH$_2$— group can optionally be replaced by a —C(O)—. Preferably "carbocyclyl" is a monocyclic ring containing 5 or 6 atoms or a bicyclic ring containing 9 or 10 atoms. Suitable values for "carbocyclyl" include cyclopropyl, cyclobutyl, 1-oxocyclopentyl, cyclopentyl, cyclopentenyl, cyclohexyl, cyclohexenyl, phenyl, naphthyl, tetralinyl, indanyl or 1-oxoindanyl. Particularly "carbocyclyl" is cyclopropyl, cyclobutyl, 1-oxocyclopentyl, cyclopentyl, cyclopentenyl, cyclohexyl, cyclohexenyl, phenyl or 1-oxoindanyl.

An example of "$C_{1-10}$alkanoyloxy" and "$C_{1-6}$alkanoyloxy" is acetoxy. Examples of "$C_{1-10}$alkoxycarbonyl" and "$C_{1-6}$alkoxycarbonyl" include methoxycarbonyl, ethoxycarbonyl, n- and t-butoxycarbonyl. Examples of "$C_{1-10}$alkoxy" and "$C_{1-6}$alkoxy" include methoxy, ethoxy and propoxy. Examples of "$C_{1-10}$alkanoylamino" and "$C_{1-6}$alkanoylamino" include formamido, acetamido and propionylamino. Examples of "$C_{1-10}$alkylS(O)$_a$ wherein a is 0 to 2" and "$C_{1-6}$alkylS(O)$_a$ wherein a is 0 to 2" include methylthio, ethylthio, methylsulphinyl, ethylsulphinyl, mesyl and ethylsulphonyl. Examples of "$C_{1-10}$alkanoyl" and "$C_{1-6}$alkanoyl" include $C_{1-3}$alkanoyl, propionyl and acetyl. Examples of "N—$C_{1-10}$alkylamino" and "N—$C_{1-6}$alkylamino" include methylamino and ethylamino. Examples of "N,N—($C_{1-10}$alkyl)$_2$amino" and "N,N—($C_{1-6}$alkyl)$_2$amino" include di-N-methylamino, di-(N-ethyl)amino and N-ethyl-N-methylamino. Examples of "$C_{2-10}$alkenyl" and "$C_{2-6}$alkenyl" are vinyl, allyl and 1-propenyl. Examples of "$C_{2-10}$alkyl" and "$C_{2-6}$alkynyl" are ethynyl, 1-propynyl and 2-propynyl. Examples of "N—($C_{1-10}$alkyl)sulphamoyl" and "N—($C_{1-6}$alkyl)sulphamoyl" are N—($C_{1-3}$alkyl)sulphamoyl, N(methyl)sulphamoyl and N-ethyl)sulphamoyl. Examples of "N—($C_{1-10}$alkyl)$_2$sulphamoyl" and "N—($C_{1-6}$alkyl)$_2$sulphamoyl" are N,N-(dimethyl)sulphamoyl and N-(methyl)-N-(ethyl)sulphamoyl. Examples of "N—($C_{1-10}$alkyl)carbamoyl" and "N—($C_{1-6}$alkyl)carbamoyl" are methylaminocarbonyl and ethylaminocarbonyl. Examples of "N,N—($C_{1-10}$alkyl)carbamoyl" and "N,N—($C_{1-6}$alkyl)carbamoyl" are dimethylaminocarbonyl and methylethylaminocarbonyl. Example of "$C_{1-10}$alkylsulphonyl" and "$C_{1-6}$-alkylsulphonyl" are mesyl and ethylsulphonyl. Examples of "N,N,N—($C_{1-10}$alkyl)$_3$ammonio" and "N,N,N—($C_{1-6}$alkyl)$_3$ammonio" are trimethylamino and methyldiethylamino. Examples of "$C_{1-10}$alkoxycarbonylamino" and "$C_{1-6}$alkoxycarbonylamino" are methoxycarbonylamino and t-butoxycarbonylamino. Examples of "N—($C_{1-10}$alkyl)sulphamoylamino" and "N—($C_{1-6}$alkyl)sulphamoylamino" are N-methylsulphamoylamino and N-ethylsulphamoylamino. Examples of "N,N—($C_{1-10}$alkyl)$_2$ sulphamoylamino" and "N,N—($C_{1-6}$alkyl)$_2$sulphamoylamino" are N,N-dimethylsulphamoylamino and N-methyl-N-ethylsulphamoylamino. Examples of "$C_{1-10}$alkylthio" and "$C_{1-6}$alkylthio" are methylthio and ethylthio. Examples of "carbocyclyl$C_{1-10}$alkyl" include benzyl and phenethyl. Examples of "heterocyclyl$C_{1-10}$alkyl" include morpholinopropyl and pyridylmethyl.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric, acetate or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

The compounds of the formula (I) may be administered in the form of a pro-drug which is broken down in the human or animal body to give a compound of the formula (I). examples of pro-rugs include in vivo hydrolysable esters and in vivo hydrolysable amides of a compound of the formula (I).

An in vivo hydrolysable ester of a compound of the formula (I) containing carboxy or hydroxy group is, for example, a pharmaceutically acceptable ester which is hydrolysed in the human or animal body to produce the parent acid or alcohol. Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2onylmethyl; and $C_{1-6}$alkoxycarbonyloxyethyl esters for example 1-methoxycarbonyloxyethyl and may be formed at any carboxy group in the compounds of this invention.

An in viva hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

A suitable value for an in vivo hydrolysable amide of a compound of the formula (I) containing a carboxy group is, for example, a N—$C_{1-6}$alkyl or N,N-di-$C_{1-6}$alkyl amide such as NV-methyl, N-ethyl, N-propyl, N,N-dimethyl, N-ethyl-N-methyl or N,N-ethyl amide.

Some compounds of the formula (I) may have chiral centres and/or geometric isomeric centres (E- and Z-isomers), and it is to be understood that the invention encompasses all such optical, diastereoisomers and geometric isomers that possess IBAT inhibitory activity.

The invention relates to any and all tautomeric forms of the compounds of the formula (I) that possess IBAT inhibitory activity.

It is also to be understood that certain compounds of the formula (I) can exist in solvated as well as unsolvated forms such as, for example, hydrated forms. It is to be understood that the invention encompasses all such solvated forms which possess IBAT inhibitory activity.

Particular values are as follows. Such values may be used where appropriate with any of the definitions, claims or embodiments defined hereinbefore or hereinafter.

$R^v$ is selected from hydrogen.
$R^1$ and $R^2$ are both $C_{1-6}$alkyl.
$R^1$ and $R^2$ are both $C_{1-4}$alkyl.
One of $R^1$ and $R^2$ is ethyl and the other is butyl.
$R^1$ and $R^2$ are both butyl.
$R^x$ and $R^y$ are both hydrogen.
$R^z$ is $C_{1-4}$alkyl.
v is 0–2.
v is 0.
$R^4$ is a group of formula (IA).
$R^5$ is a group of formula (IA).
$R^3$ and $R^6$ are hydrogen.

$R^4$ is halo.

$R^4$ is bromo or chloro.

$R^4$ is $C_{1-6}$alkoxy.

$R^4$ is ethoxy or methoxy.

$R^4$ is methoxy.

$R^4$ is ethylthio or methylthio.

$R^4$ is methylthio.

$R^5$ is methylthio.

$R^5$ is a group of formula (IA) and $R^4$ is $C_{1-6}$alkylS(O)$_a$ wherein a is 0.

$R^5$ is a group of formula (IA) and $R^4$ is $C_{1-4}$alkylS(O)$_a$ wherein a is 0.

$R^5$ is a group of formula (IA) and $R^4$ is methylthio.

X is —O—.

Ring A is aryl; wherein Ring A is optionally substituted on carbon by one or more substituents selected from $R^{18}$; wherein $R^{18}$ is hydroxy.

Ring A is phenyl; wherein Ring A is optionally substituted on carbon by one or more substituents selected from $R^{18}$; wherein $R^{18}$ is hydroxy.

Ring A is phenyl or 4hydroxyphenyl.

$R^7$ is hydrogen.

$R^8$ is hydrogen.

$R^9$ is hydrogen.

$R^{10}$ is a group of formula (IB).

$R^{11}$ is hydrogen.

$R^{12}$ and $R^{13}$ are independently selected from hydrogen or $C_{1-10}$alkyl.

$R^{12}$ and $R^{13}$ are independently selected from hydrogen or $C_{1-4}$alkyl.

$R^{12}$ and $R^{13}$ as independently selected from hydrogen or methyl.

$R^{12}$ and $R^{13}$ are both hydrogen or one of $R^{12}$ and $R^{13}$ is hydrogen and the other is methyl.

$R^{14}$ is selected from $C_{1-10}$alkyl or carbocyclyl$C_{1-10}$alkyl; wherein $R^{14}$ may be optionally substituted on carbon by one or more substituents selected from $R^{29}$; wherein $R^{29}$ is hydroxy.

$R^{14}$ is selected from $C_{1-10}$alkyl, carbocyclyl$C_{1-10}$alkyl and heterocyclyl$C_{1-10}$alkyl; wherein $R^{14}$ may be optionally substituted on carbon by one or more substituents selected from $R^{29}$; wherein $R^{29}$ is hydroxy; or $R^{14}$ is a group of formula (IC) (as depicted above).

$R^{14}$ is selected from $C_{1-6}$alkyl or phenyl$C_{1-4}$alkyl; wherein $R^{14}$ may be optionally substituted on carbon by one or more substituents selected from $R^{29}$; wherein $R^{29}$ is hydroxy.

$R^{14}$ is selected from pentyl, benzyl and tetrahydropyran; wherein $R^{14}$ may be optionally substituted on carbon by one or more substituents selected from $R^{29}$; wherein $R^{29}$ is hydroxy; or $R^{14}$ is a group of formula (IC) (as depicted above).

$R^{14}$ is selected from pentyl or benzyl; wherein $R^{14}$ may be optionally substituted on carbon by one or more substituents selected from $R^{29}$; wherein $R^{29}$ is hydroxy.

$R^{14}$ is selected from 1,2,3,4,5-pentahydroxypentyl or 3,4-dihydroxybenzyl.

$R^{15}$ and $R^{16}$ together with the nitrogen to which they are attached form a heterocyclyl; wherein said heterocyclyl may be optionally substituted on carbon by one or more $R^{37}$; wherein $R^{37}$ is N—($C_{1-10}$alkyl)carbamoyl; optionally substituted on carbon by one or more $R^{34}$; wherein $R^{34}$ is carbamoyl.

$R^{15}$ and $R^{16}$ together with the nitrogen to which they are attached form pyrrolidinyl; wherein said pyrrolidinyl may be optionally substituted on carbon by one or more $R^{37}$; $R^{37}$ is N-methylcarbamoyl; optionally substituted on carbon by one or more $R^{34}$; wherein $R^{34}$ is carbamoyl.

$R^{15}$ and $R^{16}$ together with the nitrogen to which they are attached form 2(N-(carbamoylmethyl)carbamoylpyrrolidin-1-yl.

n is 1.

$R^5$ is a group of formula (IA) as depicted above wherein:

X is —O—;

$R^7$ is hydrogen;

$R^8$ is hydrogen;

$R^9$ is hydrogen;

Ring A is aryl;

$R^{10}$ is carbamoyl or N—($C_{1-10}$alkyl)carbamoyl or a group of formula (IB) (as depicted above) wherein $R^{10}$ is optionally substituted on carbon by one or more substituents selected from $R^{23}$ and wherein:

$R^{11}$ is hydrogen;

$R^{12}$ and $R^{13}$ are independently selected from hydrogen, carbamoyl or $C_{1-6}$alkyl; wherein $R^{12}$ and $R^{13}$ may be independently optionally substituted on carbon by one or more substituents selected from $R^{25}$;

$R^{14}$ is selected from carbamoyl, hydroxyaminocarbonyl, $C_{1-6}$alkyl, carbocyclyl, carbocyclyl$C_{1-10}$alkyl, heterocyclyl, heterocyclyl$C_{1-10}$alkyl or carbocyclyl-$C_{1-6}$alkylene)$_p$-$R^{27}$—($C_{1-6}$alkylene)$_q$-; wherein $R^{14}$ may be optionally substituted on carbon by one or more substituents selected from $R^{29}$; and wherein if said heterocyclyl contains an —NH— group, that nitrogen may be optionally substituted by a group selected from $R^{30}$; or $R^{14}$ is a group of formula (IC) (as depicted above) wherein:

$R^{15}$ is hydrogen or $C_{1-6}$alkyl;

$R^{16}$ is $C_{1-6}$alkyl; wherein $R^{16}$ may be optionally substituted on carbon by one or more groups selected from $R^{31}$;

n is 1;

$R^{23}$ is hydroxy;

$R^{25}$, $R^{29}$ or $R^{31}$ are independently selected from halo, hydroxy, amino, sulphamoyl, $C_{1-6}$alkoxy, N,N,N—($C_{1-6}$alkyl)$_3$ammonio, N,N—($C_{1-6}$alkyl)$_2$sulphamoylamino, $C_{1-6}$alkoxycarbonylamino, carbocyclyl, heterocyclyl, carbocyclyl-($C_{1-6}$alkylene)$_p$-$R^{32}$—($C_{1-6}$alkylene)$_q$- or heterocyclyl-$C_{1-6}$alkylene)$_r$-$R^{33}$—($C_{1-6}$alkylene)$_s$-; wherein $R^{25}$, $R^{29}$ or $R^{31}$ may be independently optionally substituted on carbon by one or more $R^{34}$; and wherein if said heterocyclyl contains an —NH— group, that nitrogen may be optionally substituted by a group selected from $R^{35}$;

$R^{27}$, $R^{32}$ or $R^{33}$ are independently selected from —O—, —NR$^{36}$C(O)NR$^{36}$—, —OC(O)N=C—or —NR$^{36}$C(O)—; wherein $R^{23}$ is hydrogen;

p, q, r and s are independently selected from 0 or 1;

$R^{34}$ is selected from hydroxy, amino, carbamoyl, sulphamoyl or methoxy;

$R^{30}$ or $R^{35}$ are independently selected from $C_{1-6}$alkyl or $C_{1-6}$alkoxycarbonyl.

$R^5$ is a group of formula (IA) as depicted above wherein:

X is —O—;

Ring A is aryl; wherein Ring A is optionally substituted on carbon by one or more substituents selected from $R^{18}$;

$R^7$ is hydrogen;

$R^8$ is hydrogen;

$R^9$ is hydrogen;

$R^{10}$ is a group of formula (IB) (as depicted above):

$R^{11}$ is hydrogen;

$R^{12}$ and $R^{13}$ are independently selected from hydrogen or $C_{1-10}$alkyl;

$R^{14}$ is selected from $C_{1-10}$alkyl, carbocyclyl$C_{1-10}$alkyl and heterocyclyl; wherein $R^{14}$ may be optionally substituted on carbon by one or more substituents selected from $R^{29}$; or $R^{14}$ is a group of formula (IC) (as depicted above);

$R^{15}$ and $R^{16}$ together with the nitrogen to which they are attached form a heterocyclyl; wherein said heterocyclyl may be optionally substituted on carbon by one or more $R^{37}$;

n is 1;

$R^{18}$, $R^{29}$ and $R^{37}$ are independently selected from hydroxy and N—($C_{1-10}$-alkyl)carbamoyl; wherein $R^{18}$, $R^{29}$ and $R^{37}$ may be independently optionally substituted on carbon by one or more $R^{34}$; and $R^{34}$ is carbamoyl.

$R^5$ is a group of formula (IA) as depicted above wherein:

X is —O—;

$R^7$ is hydrogen;

$R^8$ is hydrogen;

$R^9$ is hydrogen;

Ring A is phenyl;

$R^{10}$ is carbamoyl or a group of formula (IB) (as depicted above) wherein:

$R^{11}$ is hydrogen;

$R^{12}$ and $R^{13}$ are independently selected from hydrogen, carbamoyl or $C_{1-6}$alkyl; wherein $R^{12}$ and $R^{13}$ may be independently optionally substituted on carbon by one or more substituents selected from $R^{25}$;

$R^{14}$ is selected from carbamoyl, hydroxyaminocarbonyl, $C_{1-6}$alkyl, carbocyclyl, heterocyclyl or carbocyclyl-($C_{1-6}$alkylene)$_p$-$R^{27}$—($C_{1-6}$alkylene)$_q$-; wherein $R^{14}$ may be optionally substituted on carbon by one or more substituents selected from $R^{29}$; and wherein if said heterocyclyl contains an —NH— group, that nitrogen may be optionally substituted by a group selected from $R^{30}$; or $R^{14}$ is a group of formula (IC) (as depicted above) wherein:

$R^{15}$ is hydrogen;

$R^{16}$ is $C_{1-6}$alkyl; wherein $R^{16}$ may be optionally substituted on carbon by one or more groups selected from $R^{31}$;

n is 1;

$R^{25}$, $R^{29}$ or $R^{31}$ are independently selected from halo, hydroxy, amino, sulphamoyl, $C_{1-6}$alkoxy, N,N,N—($C_{1-6}$alkyl)$_3$ammonio, N,N—($C_{1-6}$alkyl)$_2$sulphamoylamino, $C_{1-6}$alkoxycarbonylamino, carbocyclyl, heterocyclyl, carbocyclyl-($C_{1-6}$alkylene)$_p$-$R^{32}$—($C_{1-6}$alkylene)$_q$- or heterocyclyl-($C_{1-6}$alkylene)$_r$-$R^{33}$—($C_{1-6}$alkylene)$_s$-; wherein $R^{25}$, $R^{29}$ or $R^{31}$ may be independently optionally substituted on carbon by one or more $R^{34}$; and wherein if said heterocyclyl contains an —NH— group, that nitrogen may be optionally substituted by a group selected from $R^{35}$;

$R^{27}$, $R^{32}$ or $R^{33}$ are independently selected from —O—, —NR$^{36}$C(O)NR$^{36}$—, —OC(O)N═C— or —NR$^{36}$C(O)—; wherein $R^{23}$ is hydrogen;

p, q, r and s are independently selected from 0 or 1;

$R^{34}$ is selected from hydroxy, amino, carbamoyl, sulphamoyl or methoxy;

$R^{30}$ or $R^{35}$ are independently selected from $C_{1-6}$alkyl or $C_{1-6}$alkoxycarbonyl.

$R^5$ is a group of formula (IA) as depicted above wherein:

X is —O—;

$R^7$ is hydrogen;

$R^8$ is hydrogen;

$R^9$ is hydrogen;

$R^{10}$ is carbamoyl or a group of formula (IB) (as depicted above) wherein:

$R^{11}$ is hydrogen;

$R^{12}$ and $R^{13}$ are independently selected from hydrogen, carbamoyl or methyl; wherein $R^{12}$ and $R^{13}$ may be independently optionally substituted on carbon by one or more substituents selected from $R^{25}$;

$R^{14}$ is selected from carbamoyl, hydroxyaminocarbonyl, methyl, ethyl, propyl, phenyl, 1,5-benzodioxepinyl, 2,3-dihydrobenzofuranyl, piperidinyl, anilinocarbonyl or anilinocarbonyl; wherein $R^{14}$ may be optionally substituted on carbon by one or more substituents selected from $R^{29}$; and wherein said piperidinyl may be optionally substituted on nitrogen by a group selected from $R^{30}$; or $R^{14}$ is a group of formula (IC) (as depicted above) wherein:

$R^{15}$ is hydrogen;

$R^{16}$ is methyl, ethyl or hexyl; wherein $R^{16}$ may be optionally substituted on carbon by one or more groups selected from $R^{31}$;

n is 1;

$R^{25}$, $R^{29}$ or $R^{31}$ are independently selected from fluoro, hydroxy, amino, sulphamoyl, methoxy, N,N,N-trimethylamino, N,N-dimethylsulphamoylamino, t-butoxycarbonylamino, phenyl, morpholino, imidazolyl, indolyl, 2,4thiazolidinedionyl, piperazinyl, 2-imidazolidinonyl, phenoxy, benxyloxycarbonyliminomethyl, N'-pyridinylureido or N'-pyrimidinylureido; wherein $R^{25}$, $R^{29}$ or $R^{31}$ may be independently optionally substituted on carbon by one or more $R^{34}$; and wherein said imidazolyl, indolyl, piperazinyl or 2-imidazolidinonyl may be optionally substituted on nitrogen by a group selected from $R^{35}$;

$R^{27}$, $R^{32}$ or $R^{33}$ are independently selected from —O—, —NHC(O)NH—, —OC(O)N═C— or —NHC(O)—;

p, q, r and s are independently selected from 0 or 1;

$R^{34}$ is selected from hydroxy, amino, carbamoyl, sulphamoyl or methoxy;

$R^{30}$ or $R^{35}$ are independently selected from methyl or $C_{1-6}$alkoxycarbonyl.

$R^5$ is a group of formula (IA) as depicted above wherein:

X is —O—;

Ring A is phenyl; wherein Ring A is optionally substituted on carbon by one or more substituents selected from $R^{18}$;

$R^7$ is hydrogen;

$R^8$ is hydrogen;

$R^9$ is hydrogen;

$R^{10}$ is a group of formula (IB) (as depicted above):

$R^{11}$ is hydrogen;

$R^{12}$ and $R^{13}$ are independently selected from hydrogen or methyl;

$R^{14}$ is selected from pentyl, benzyl and tetrahydropyran; wherein $R^{14}$ may be optionally substituted on carbon by one or more substituents selected from $R^{29}$; or $R^{14}$ is a group of formula (IC) (as depicted above);

$R^{15}$ and $R^{16}$ together with the nitrogen to which they are attached form pyrrolidinyl; wherein said pyrrolidinyl may be optionally substituted on carbon by one or more $R^{37}$;

n is 1;

$R^{18}$, $R^{29}$ and $R^{37}$ are independently selected from hydroxy and N-methylcarbamoyl; wherein $R^{18}$, $R^{29}$ and $R^{37}$ may be independently optionally substituted on carbon by one or more $R^{34}$; and $R^{34}$ is carbamoyl.

$R^5$ is selected from:

N-{(R)-α-[N'-(2-hydroxyethyl)carbamoyl]benzyl}carbamoylmethoxy;

N-{(R)-α-[N'-(2-trimethylaminoethyl)carbamoyl]benzyl}carbamoylmethoxy;

N-{(R)-α-[N'-(2-aminoethyl)carbamoyl]benzyl}carbamoylmethoxy;

N-{(R)-α-[N'-(carbamoylmethyl)carbamoyl]benzyl}carbamoylmethoxy;

N-{(R)-α-[N'—((S)-1-carbamoyl-2-hydroxyethyl)carbamoyl]benzyl}carbamoylmethoxy;

N-((R)-α-carbamoylbenzyl)carbamoylmethoxy;

N-{(R)-α-[N'-(1,1-di-hydroxymethyl-2-hydroxyethyl)carbamoyl]benzyl}carbamoylmethoxy;
N-{(R)-α-[N'-(hydroxycarbamoylmethyl)carbamoyl]benzyl}carbamoylmethoxy;
N-((R)-α-{N'-[N-(2,2,2-trifluoroethyl)carbamoylmethyl]carbamoyl}benzyl) carbamoylmethoxy;
N-((R)-α-{N'-[N-(2-(S)-3-(R)-4-(R)-5-(R)-2,3,4,5,6-pentahydroxyhexyl)carbamoylmethyl]carbamoyl}benzyl) carbamoylmethoxy;
N-((R)-α-{N'-[N-(2-fluoroethyl)carbamoylmethyl]carbamoyl}benzyl)carbamoylmethoxy;
N-((R)-α-{N'-[N-(ethyl)carbamoylmethyl]carbamoyl}benzyl)carbamoylmethoxy;
N-((R)-α-{N'-[N-(4-hydroxy-3-methoxybenzyl)carbamoylmethyl]carbamoyl}benzyl) carbamoylmethoxy,
N-((R)-α-{N'-[N-(2-methoxyethyl)carbamoylmethyl]carbamoyl}benzyl)carbamoylmethoxy;
N-((R)-α-{N'-[N-(4-sulphamoylphenethyl)carbamoylmethyl]carbamoyl}benzyl) carbamoylmethoxy;
N-((R)-α-{N'-[N-(2-N,N-dimethylaminosulphamoylethyl)carbamoylmethyl]carbamoyl}benzyl)carbamoylmethoxy;
N-[(R)-α-(N'-(N-[2-(N'-pyrimidin-2-ylreido)ethyl]carbamoylmethyl}carbamoyl)benzyl]carbamoylmethoxy;
(N-{(R)-α-[N'-(2-(S)-3-(R)-4-(R)-5-(R)-3,4,5,6-pentahydroxyhexyl)carbamoyl]benzyl}carbamoylmethoxy;
N-{(R)-α-[N'-3-morpholinopropyl)carbamoyl]benzyl}carbamoylmethoxy;
N-{(R)-α-[N'-(2-imidazol-4-ylethyl)carbamoyl]benzyl}carbamoylmethoxy;
N-{(R)-α-[N'-(2-N,N-dimethylaminosulphamoylethyl)carbamoyl]benzyl}carbamoylmethoxy;
N-((R)-α-{N'-[2-(2-hydroxyphenoxy)ethyl]carbamoyl}benzyl)carbamoylmethoxy;
N-{(R)-α-[N'-(3-hydroxy-1,5-benzodioxepin-3-ylmethyl)carbamoyl]benzyl}carbamoylmethoxy;
N-{(R)-α-[N'-3-t-butoxycarbonylaminobenzyl)carbamoyl]benzyl}carbamoylmethoxy;
N-((R)-α-{N'-[3-(benxyloxycarbonylimino-1-aminomethyl)benzyl]carbamoyl}benzyl) carbamoylmethoxy;
N-((R)-α-{N'-[2-(3,4-dihydroxyphenyl-2-methoxyethyl]carbamoyl}benzyl) carbamoylmethoxy;
N-{(R)-α-[N'-(2,3-dihydroxypropyl)carbamoyl]benzyl}carbamoylmethoxy;
N-((R)-α-{N'-[2-(5-methoxyindol-3-yl)ethyl]carbamoyl}benzyl)carbamoylmethoxy;
N-((R)-α-{N'-[2-(2,5-dioxothiazolidin-1-yl)ethyl]carbamoyl}benzyl)carbamoylmethoxy;
N-((R)-α-{N'-[3-(-methylpiperazin-1-yl)propyl]carbamoyl}benzyl)carbamoylmethoxy;
N-{(R)-α-[N'-(4-sulphamoylphenethyl)carbamoyl]benzyl}carbamoylmethoxy;
N-{(R)-α-[N'-(5,6-dimethoxy-2,3-dihydobenzofuran-2-ylmethyl)carbamoyl]benzyl}carbamoylmethoxy;
N-{(R)-α-[N'-(1-t-butoxycarbonylpiperidin-4ylmethyl)carbamoyl]benzyl}carbamoylmethoxy;
N-{(R)-α-[N'-(4-nitroanilinocarbonylmethyl)carbamoyl]benzyl}carbamoylmethoxy;
N-((R)-α-{N'-[2-(N'-pyrimidin-2-ylreido)ethyl]carbamoyl}benzyl)carbamoylmethoxy;
N-((R)-α-{N'-[2-(N'-pyridin-2-ylreido)ethyl]carbamoyl}benzyl)carbamoylmethoxy;
N-((R)-α-{N'-[2-(4-carbamoylphenoxy)ethyl]carbamoyl}benzyl)carbamoylmethoxy;
N-((R)-α-{N'-[2-(2-oxoimidazolidin-1-yl)ethyl]carbamoyl}benzyl)carbamoylmethoxy; and
N-{(R)-α-[N'-(3-aminobenzyl)carbamoyl]benzyl}carbamoylmethoxy.

$R^5$ is selected from:
N-{(R)-α-[N-(2-(S)-3-(R)-5-(R)-2,3,4,5,6-pentahydroxyhexyl)carbamoyl]benzyl}carbamoylmethoxy;
N-{(R)-α-[N-(2-(S)-3-(R)-4-(R)-5-(R)-2,3,4,5,6-pentahydroxyhexyl)carbamoyl]-4-hydroxybenzyl}carbamoylmethoxy;
N-((R/S)-α-{N-[1-(R)-2-(S)-1-hydroxy-1-(3,4-dihydroxyphenyl)prop-2-yl]carbamoyl}-4-hydroxybenzyl)carbamoylmethoxy;
N-[(R)-α-(N-{2-(S)[N-(carbamoylmethyl)carbamoyl]pyrrolidin-1-ylcarbonylmethyl}carbamoyl)benzyl]carbamoylmethoxy;
N-((R)-α-{N-[2-(3,4,5-trihydroxyphenyl)ethyl]carbamoyl}benzyl)carbamoylmethoxy; and
N-{(R)-α-[N-(2-(R)-3-(S)-4-(S)-5-R)-3,4,5,6-tetrahydroxytetrahyropyran-2-ylmethyl)carbamoyl]benzyl}carbamoylmethoxy.

Therefore in a further aspect of the invention there is provided a compound of formula (I) wherein:
$R^v$ is selected from hydrogen;
$R^1$ and $R^2$ are both $C_{1-6}$alkyl;
$R^x$ and $R^y$ are both hydrogen;
v is 0;
$R^3$ and $R^6$ are both hydrogen;
$R^5$ is a group of formula (IA) and $R^4$ is $C_{1-6}$alkylS(O)$_a$ wherein a is 0;
X is —O—;
Ring A is aryl; wherein Ring A is optionally substituted on carbon by one or more substituents selected from $R^{18}$; wherein $R^{18}$ is hydroxy;
$R^7$ is hydrogen;
$R^8$ is hydrogen;
$R^9$ is hydrogen;
$R^{10}$ is a group of formula (IB);
$R^{11}$ is hydrogen;
$R^{12}$ and $R^{13}$ are independently selected from hydrogen or $C_{1-10}$alkyl;
$R^{14}$ is selected from $C_{1-10}$alkyl or carbocyclyl$C_{1-10}$alkyl; wherein $R^{14}$ may be optionally substituted on carbon by one or more substituents selected from $R^{29}$; wherein $R^{29}$ is hydroxy, or a pharmaceutically acceptable salt, solvate, solvate of such a salt or a prodrug thereof.

Therefore in a further aspect of the invention there is provided a compound of formula (I) wherein:
$R^v$ is selected from hydrogen;
$R^1$ and $R^2$ are both $C_{1-6}$allyl;
$R^x$ and $R^y$ are both hydrogen;
v is 0;
$R^3$ and $R^6$ are both hydrogen;
$R^5$ is a group of formula (IA) and $R^4$ is $C_{1-6}$alkylS(O)$_a$ wherein a is 0;
X is —O—;
Ring A is aryl; wherein Ring A is optionally substituted on carbon by one or more substituents selected from $R^{18}$;
$R^7$ is hydrogen;
$R^8$ is hydrogen;
$R^9$ is hydrogen;
$R^{10}$ is a group of formula (IB) (as depicted above):
$R^{11}$ is hydrogen;
$R^{12}$ and $R^{13}$ are independently selected from hydrogen or $C_{1-10}$alkyl;
$R^{14}$ is selected from $C_{1-10}$alkyl, carbocyclyl$C_{1-10}$alkyl and heterocyclyl; wherein $R^{14}$ may be optionally substituted on carbon by one or more substituents selected from $R^{29}$; or $R^{14}$ is a group of formula (IC) (as depicted above);

$R^{15}$ and $R^{16}$ together with the nitrogen to which they are attached form a heterocyclyl; wherein said heterocyclyl may be optionally substituted on carbon by one or more $R^{37}$;

n is 1;

$R^{18}$, $R^{29}$ and $R^{37}$ are independently selected from hydroxy and N—($C_{1-10}$alkyl)carbamoyl; wherein $R^{18}$, $R^{29}$ and $R^{37}$ maybe independently optionally substituted on carbon by one or more $R^{34}$; and $R^{34}$ is carbamoyl;

or a pharmaceutically acceptable salt, solvate, solvate of such a salt or a prodrug thereof.

Therefore in another aspect of the invention there is provided a compound of formula (I) wherein:

$R^v$ is selected from hydrogen;

$R^1$ and $R^2$ are both butyl;

$R^x$ and $R^y$ are both hydrogen;:

v is 0;

$R^3$ and $R^6$ are both hydrogen;

$R^5$ is a group of formula (IA) and $R^4$ is methylthio;

X is —O—;

Ring A is phenyl or 4-hydroxyphenyl;

$R^7$ is hydrogen;

$R^8$ is hydrogen;

$R^9$ is hydrogen;

$R^{10}$ is a group of formula (IB);

$R^{11}$ is hydrogen;

$R^{12}$ and $R^{13}$ are both hydrogen or one of $R^{12}$ and $R^{13}$ is hydrogen and the other is methyl;

$R^{14}$ is selected from 1,2,3,4,5-pentahydroxypentyl or 3,4-dihydroxybenzyl;

or a pharmaceutically acceptable salt, solvate, solvate of such a salt or a prodrug thereof.

Therefore in another aspect of the invention there is provided a compound of formula (I) wherein:

$R^v$ is selected from hydrogen;

$R^1$ and $R^2$ are both butyl;

$R^x$ and $R^y$ are both hydrogen;

v is 0;

$R^3$ and $R^6$ are both hydrogen;

$R^5$ is a group of formula (IA) and $R^4$ is methylthio;

X is —O—;

Ring A is phenyl; wherein Ring A is optionally substituted on carbon by one or more substituents selected from $R^{18}$;

$R^7$ is hydrogen;

$R^8$ is hydrogen;

$R^9$ is hydrogen;

$R^{10}$ is a group of formula (IB) (as depicted above):

$R^{11}$ is hydrogen;

$R^{12}$ and $R^{13}$ are independently selected from hydrogen or methyl;

$R^{14}$ is selected from pentyl, benzyl and tetrahydropyran; wherein $R^{14}$ may be optionally substituted on carbon by one or more substituents selected from $R^{29}$; or $R^{14}$ is a group of formula (IC) (as depicted above);

$R^{15}$ and $R^{16}$ together with the nitrogen to which they are attached form pyrrolidinyl;

wherein said pyrrolidinyl may be optionally substituted on carbon by one or more $R^{37}$;

n is 1;

$R^{18}$, $R^{29}$ and $R^{37}$ are independently selected from hydroxy and N-methylcarbamoyl;

wherein $R^{18}$, $R^{29}$ and $R^{37}$ may be independently optionally substituted on carbon by one or more $R^{34}$; and $R^{34}$ is carbamoyl;

or a pharmaceutically acceptable salt, solvate, solvate of such a salt or a prodrug thereof.

Therefore in another aspect of the invention there is provided a compound of formula (I) wherein:

$R^v$ is selected from hydrogen;

$R^1$ and $R^2$ are both butyl;

$R^x$ and $R^y$ are both hydrogen;

v is 0;

$R^3$ and $R^6$ are both hydrogen;

$R^4$ is methylthio; and $R^5$ is selected from:

N-{(R)-α-[N-(2-(S)-3-(R)-4-(R)-5-(R)-2,3,4,5,6-pentahydroxyhexyl)carbamoyl]benzyl}carbamoylmethoxy;

N-{(R)-α-[N-(2-(S)-3-(R)-4-(R)-5-(R)-2,3,4,5,6-pentahydroxyhexyl)carbamoyl]-4-hydroxybenzyl}carbamoylmethoxy;

N-((R/S)-α-{N-[1-(R)-2-(S)-1-hydroxy-1-(3,4-dihydroxyphenyl)prop-2-yl]carbamoyl}-4-hydroxybenzyl)carbamoylmethoxy;

N-[(R)-α-(N-{2-(S)-[N-(carbamoylmethyl)carbamoyl]pyrrolidin-1-ylcarbonylmethyl}carbamoyl)benzyl]carbamoylmethoxy;

N-((R)-α-{N-[2-3,4,5-trihydroxyphenyl)ethyl]carbamoyl}benzyl)carbamoylmethoxy; and N-{(R)-α-[N-(2-(R)-3-(S)-4-(S)-5-(R)-3,4,5,6-tetrahydroxytetrahydropyran-2-ylmethyl)carbamoyl]benzyl}carbamoylmethoxy;

or a pharmaceutically acceptable salt, solvate, solvate of such a salt or a prodrug thereof.

In another aspect of the invention, preferred compounds of the invention are any one of the examples or a pharmaceutically acceptable salt, solvate, solvate of such a salt or a prodrug thereof.

Preferred aspects of the invention are those which relate to the compound of formula (I) or a pharmaceutically acceptable salt thereof.

Another aspect of the present invention provides a process for preparing a compound of formula (I) or a pharmaceutically acceptable salt, solvate, solvate of such a salt or a prodrug thereof which process (wherein variable groups are, unless otherwise specified, as defined in formula (I)) comprises of:

Process 1): for compounds of formula (I) wherein X is —O—, —$NR^a$ or —S—; reacting a compound of formula (IIa) or (IIb):

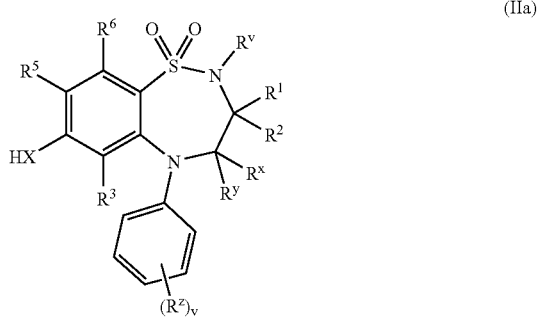

-continued

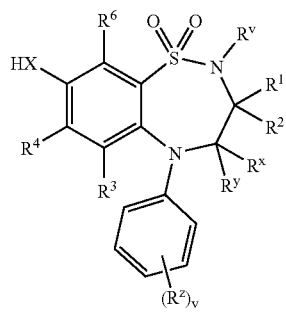

with a compound of formula (III):

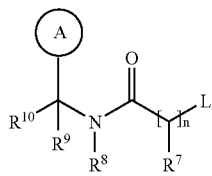

wherein L is a displaceable group;

Process 2): reacting an acid of formula (IVa) or (IVb):

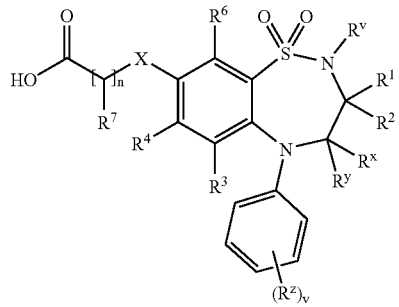

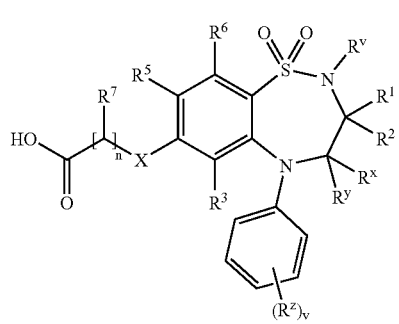

or an activated derivative thereof, with an amine of formula (V):

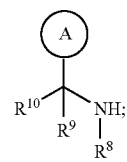

Process 3): for compounds of formula (I) wherein $R^{10}$ is a group of formula (IB); reacting a compound of formula (VIa):

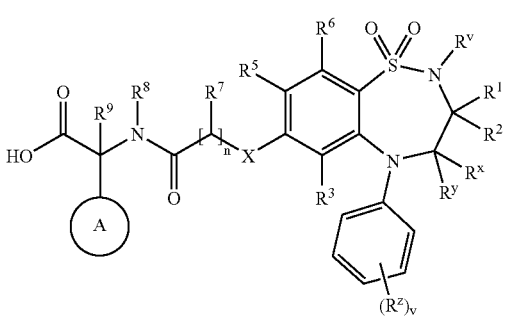

or (VIb):

(VIb)

with an amine of formula (VII):

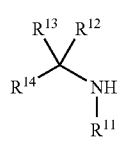

Process 4) for compounds of formula (I) wherein one of $R^4$ and $R^5$ are independently selected from $C_{1-6}$alkylthio optionally substituted on carbon by one or more $R^{17}$; reacting a compound of formula (VIIIa) or (VIIIb):

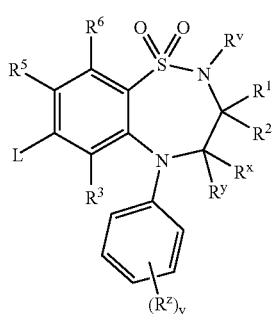

(VIIIa)

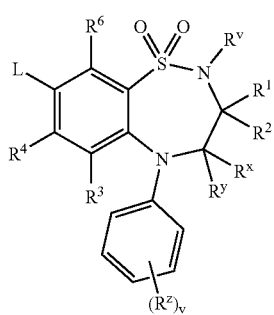

(VIIIb)

wherein L is a displaceable group; with a thiol of formula (IX):

R'''—H     (IX)

wherein R''' is $C_{1-6}$alkylthio optionally substituted on carbon by one or more $R^{17}$; or Process 5): for compounds of formula (I) wherein $R^{14}$ is a group of formula (IC); reacting a compound of formula (Xa):

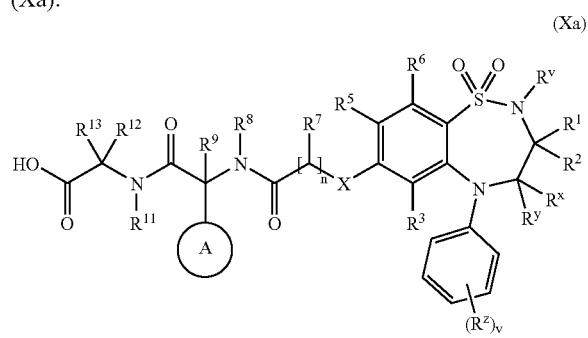

(Xa)

or (Xb):

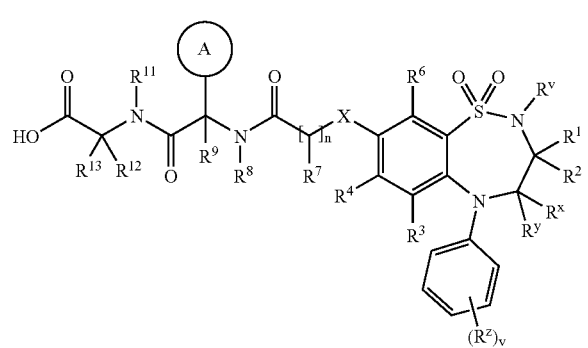

(Xb)

with an amine of formula (XI):

(XI)

and thereafter if necessary or desirable:
i) converting a compound of the formula (I) into another compound of the formula (I); and/or
ii) removing any protecting groups; and/or
ii) forming a pharmaceutically acceptable salt, solvate, solvate of such a salt or a prodrug.

L is a displaceable group, suitable values for L are for example, a halogeno or sulphonyloxy group, for example a chloro, bromo, methanesulphonyloxy or toluene-4-sulphonyloxy group.

Specific reaction conditions for the above reactions are as follows.

The bicyclic ring systems of the present invention may be assembled according the following scheme. The skilled person will appreciate to make any of the above identified intermediates the value of $R^4$ or $R^5$ in the following schemes would be replaced with the appropriate group. For example, to synthesis a compound of formula (IIa) $R^4$ would be HX in the following scheme.

Scheme 1a

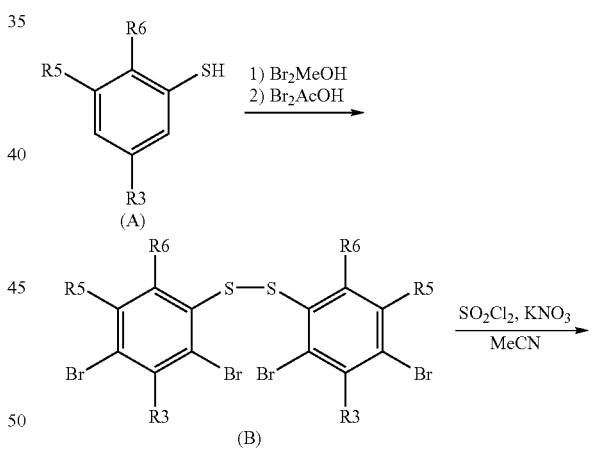

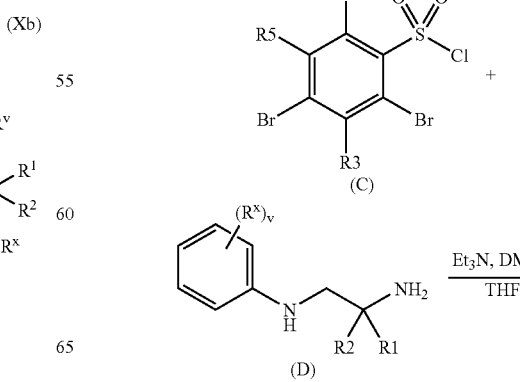

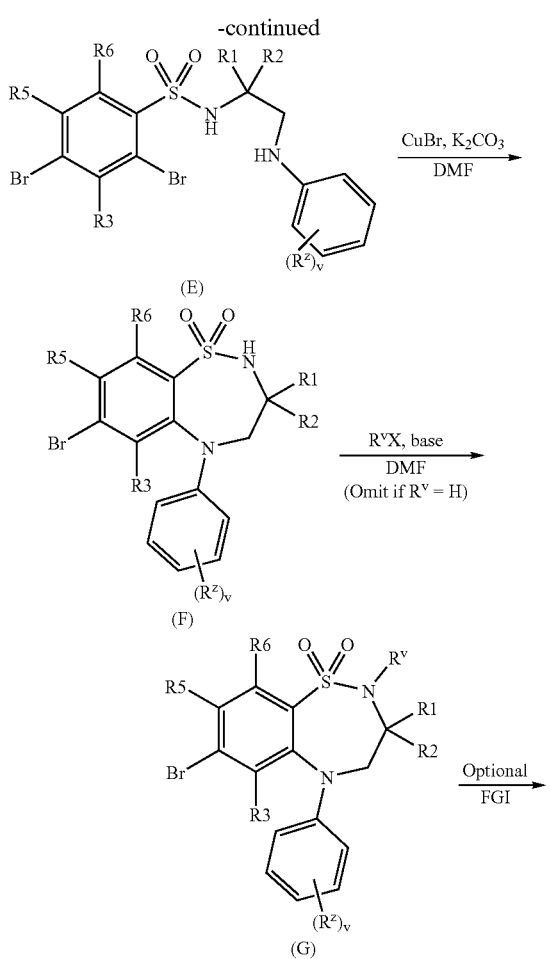

FGI is functional interconversion of the Br into other values of R⁴ using procedures known to the skilled person.

Compounds of formula (A) and (D) are commercially available, or they are known in the literature, or they may be prepared by standard processes known in the art Process 1): Compounds of formula (IIa) or (IIb) may be reacted with compounds of formula (III) in the presence of a base for example an inorganic base such as sodium carbonate, or an organic base such as Hunigs base, in the presence of a suitable solvent such as acetonitrile, dichloromethane or tetrahydrofuran at a temperature in the range of 0° C. to reflux, preferably at or near reflux.

Compounds of formula (III) are commercially available compounds, or they are known in the literature, or they are prepared by standard processes known in the art Process 2) process 3) and Process 5): Acids and amines may be coupled together in the presence of a suitable coupling reagent. Standard peptide coupling reagents known in the art can be employed as suitable coupling reagents, or for example carbonyldiimidazole and dicyclohexyl-carbodiimide, optionally in the presence of a catalyst such as dimethylaminopyridine or 4-pyrrolidinopyridine, optionally in the presence of a base for example triethylamine, pyridine, or 2,6-di-alkyl-pyridines such as 2,6-lutidine or 2,6-di-tert-butylpyridine. Suitable solvents include dimethylacetamide, dichloromethane, benzene, tetrahydrofuran and dimethylformamide. The coupling reaction may conveniently be performed at a temperature in the range of −40 to 40° C.

Suitable activated acid derivatives include acid halides, for example acid chlorides, and active esters, for example pentafluorophenyl esters. The reaction of these types of compounds with amines is well known in the art, for example they may be reacted in the presence of a base, such as those described above, and in a suitable solvent, such as those described above. The reaction may conveniently be performed at a temperature in the range of −40 to 40° C.

Compounds of formula (IVa) or (IVb) wherein X=—O—, —NR$^a$, —S— may be prepared according to Scheme 2:

Scheme 2

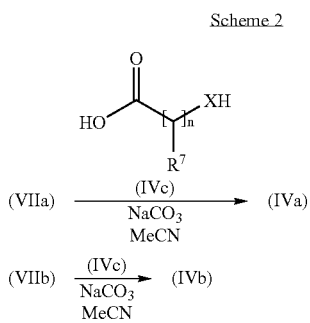

Wherein L in (VIIa) and (VIIb) is a displaceable group e.g. bromo, chloro, fluoro, mesyl or tosyl and wherein X is —O—, —S—, NR$^a$ (optionally for —SO— and —SO$_2$— followed by the oxidation step of Process 1).

Compounds of formula (IVa) and (IVb) where X is —SO— or —SO$_2$— may be prepared by oxidising the resulting compounds of formula (IVa) and (IVb) from Scheme 2 where X is —S—.

Compounds of formula (Va) or (Vb) wherein X is —CH$_2$— may be prepared according to Scheme 3.

Scheme 3

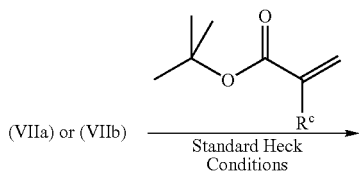

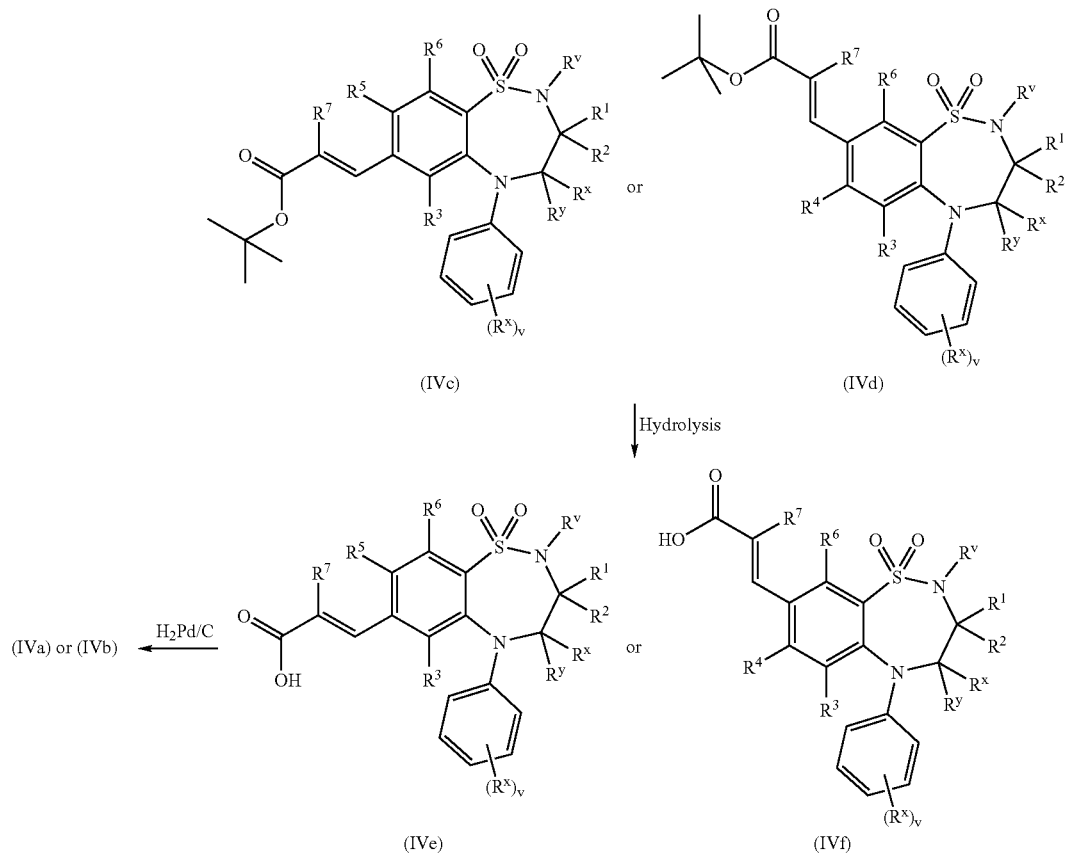

Process 4): Compounds of formula (VIIIa) and (VIIIb) may be reacted with thiols of formula (VIII) in the presence of base, for example an inorganic base such as sodium carbonate or an organic base such as Hunigs base, in the presence of a suitable solvent such as DMF or THF at a temperature in the range of 0° C. to reflux.

Compounds of formula (VIIIa) and (VIIIb) may be prepared by any of the procedures above for the preparation of compounds of formula (I), but wherein one of $R^4$ and $R^5$ is L.

Other starting materials are commercially available compounds, or they are known in the literature, or they are prepared by standard processes known in the art.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1999). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

As stated hereinbefore the compounds defined in the present invention possess IBAT inhibitory activity. These properties may be assessed, for example, using an in vitro test assay for studying the effect on bile acid uptake in IBAT-transfected cells (Smith L., Price-Jones M. J., Hugnes K. T. and Jones N. R. A.; J Biomolecular Screening, 3, 227–230) or in vivo by studying the effect on radiolabelled bile acid absorption in mice/rats (Lewis M. C., Brieaddy L. E. and Root C., J., J Lip Res 1995, 36, 1098–1105).

According to a further aspect of the invention there is provided a pharmaceutical composition which comprises a compound of formula (I), or a pharmaceutically acceptable salt, solvate, solvate of such a salt or a prodrug thereof, as defined hereinbefore in association with a pharmaceutically-acceptable diluent or carrier.

The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The compound of formula (I), or a pharmaceutically acceptable salt, solvate, solvate of such a salt or a prodrug thereof, will normally be administered to a warm-blooded animal at a unit dose within the range 5–5000 mg per square meter body area of the animal, i.e. approximately 0.1–100 mg/kg or 0.01–50 mg/kg, and this normally provides a therapeutically-effective dose. A unit dose form such as a tablet or capsule will usually contain, for example 1–250 mg of active ingredient. Preferably a daily dose in the range of 1–50 mg/kg is employed. In another aspect a daily dose in the rage of 0.02–20 mg/kg is employed. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided a compound of the formula (I), or a pharmaceutically acceptable salt, solvate, solvate of such a salt or a prodrug thereof, as defined hereinbefore for use in a method of prophylactic or therapeutic treatment of a warm-blooded animal, such as man.

We have found that the compounds defined in the present invention, or a pharmaceutically acceptable salt, solvate, solvate of such a salt or a prodrug thereof, are effective IBAT inhibitors, and accordingly have value in the treatment of disease states associated with hyperlipidaemic conditions.

Thus according to this aspect of the invention there is provided a compound of the formula (I), or a pharmaceutically acceptable salt, solvate, solvate of such a salt or a prodrug thereof, as defined hereinbefore for use as a medicament.

According to another feature of the invention there is provided the use of a compound of the formula (I), or a pharmaceutically acceptable salt, solvate, solvate of such a salt or a prodrug thereof, as defined hereinbefore in the manufacture of a medicament for use in the production of an IBAT inhibitory effect in a warm-blooded animal, such as man.

According to another feature of the invention there is provided the use of a compound of the formula (I), or a pharmaceutically acceptable salt, solvate, solvate of such a salt or a prodrug thereof, as defined hereinbefore in the manufacture of a medicament for use in the treatment of hyperlipidaemic conditions in a warm-blooded animal, such as man.

According to another feature of the invention there is provided the use of a compound of the formula (I), or a pharmaceutically acceptable salt, solvate, solvate of such a salt or a prodrug thereof, as defined hereinbefore in the manufacture of a medicament for use in the treatment of hyperlipidaemic conditions and disorders such as hyperlipidaemia, hypertrigliceridemia, hyperbetalipoproteinemia (high LDL), hyperprebetalipoproteinemia (high VLDL), hyperchylomicronemia, hypolipoproteinemia, hypercholesterolemia, hyperlipoproteinemia and hypoalphalipoproteinemia (low HDL) in a warm-blooded animal, such as man.

According to another feature of the invention there is provided the use of a compound of the formula (I), or a pharmaceutically acceptable salt, solvate, solvate of such a salt or a prodrug thereof, as defined hereinbefore in the manufacture of a medicament for use in the treatment of different clinical conditions such as atherosclerosis, arteriosclerosis, arrhythmia, hyper-thrombotic conditions, vascular dysfunction, endothelial dysfunction, heart failure, coronary heart diseases, cardiovascular diseases, myocardial infarction, angina pectoris, peripheral vascular diseases, inflammation of cardiovascular tissues such as heart, valves, vasculature, arteries and veins, aneurisms, stenosis, restenosis, vascular plaques, vascular fatty streaks, leukocytes, monocytes and/or macrophage infiltration, intimal thickening, medial thinning, infectious and surgical trauma and vascular thrombosis, stroke and transient ischaemic attacks in a warm-blooded animal, such as man.

According to another feature of the invention there is provided the use of a compound of the formula (I), or a pharmaceutically acceptable salt, solvate, solvate of such a salt or a prodrug thereof, as defined hereinbefore in the manufacture of a medicament for use in the treatment of atherosclerosis, coronary heart diseases, myocardial infarction, angina pectoris, peripheral vascular diseases, stroke and transient ischaemic attacks in a warm-blooded animal, such as man.

According to a further feature of this aspect of the invention there is provided a method for producing an IBAT inhibitory effect in a warm-blooded animal, such as man, in need of such treatment which comprises administering to said animal an effective amount of a compound of formula (I), or a pharmaceutically acceptable salt, solvate, solvate of such a salt or a prodrug thereof.

According to a further feature of this aspect of the invention there is provided a method of treating hyperlipidemic conditions in a warm-blooded animal, such as man, in need of such treatment which comprises administering to said animal an effective amount of a compound of formula (I), or a pharmaceutically acceptable salt, solvate, solvate of such a salt or a prodrug thereof.

According to a further feature of this aspect of the invention there is provided a method of treating dyslipidemic conditions and disorders such as hyperlipidaemia, hypertrigliceridemia, hyperbetalipoproteinemia (high LDL), hyperprebetalipoproteinemia (high VLDL), hyperchylomicronemia, hypolipoproteinemia, hypercholesterolemia, hyperlipoproteinemia and hypoalphalipoproteinemia (low HDL) in a warm-blooded animal, such as man, in need of such treatment which comprises administering to said animal an effective amount of a compound of formula (I), or a pharmaceutically acceptable salt, solvate, solvate of such a salt or a prodrug thereof.

According to a further feature of this aspect of the invention there is provided a method of treating different clinical conditions such as atherosclerosis, arteriosclerosis, arrhythmia, hyper-thrombotic conditions, vascular dysfunction, endothelial dysfunction, heart failure, coronary heart diseases, cardiovascular diseases, myocardial infarction, angina pectoris, peripheral vascular diseases, inflammation of cardiovascular tissues such as heart, valves, vasculature, arteries and veins, aneurisms, stenosis, restenosis, vascular plaques, vascular fatty streaks, leukocyte, monocytes and/or macrophage infiltrate, intimital thickening, medial thinning, infectious and surgical trauma and vascular thrombosis, stroke and transient ischaemic attacks in need of such treatment which comprises administering to said animal an effective amount of a compound of formula (I), or a pharmaceutically acceptable salt, solvate of such a salt or a prodrug thereof.

According to a further feature of this aspect of the invention there is provided a method of treating atherosclerosis, coronary heart diseases, myocardial infarction, angina pectoris, peripheral vascular diseases, stroke and transient ischaemic attacks in a warm-blooded animal, such as man, in need of such treatment which comprises administering to said animal an effective amount of a compound of formula (I), or a pharmaceutically acceptable salt, solvate, solvate of such a salt or a prodrug thereof.

There is evidence that an IBAT inhibitor might potentially be useful in the treatment and/or prevention of gallstones. According to a further feature of this aspect of the invention there is provided a method of treating and/or preventing gallstones in a warm-blooded animal, such as man, in need of such treatment which comprises administering to said animal an effective amount of a compound of formula (I), or a pharmaceutically acceptable salt, solvate, solvate of such a salt or a prodrug thereof.

The size of the dose required for the therapeutic or prophylactic treatment will necessarily be varied depending on the host treated, the route of administration and the severity of the illness being treated. A unit dose in the range, for example, 0.02–50 mg/kg, preferably 0.1–100 mg/kg is envisaged.

The IBAT inhibitory activity defined hereinbefore may be applied as a sole therapy or may involve, in addition to a compound of the invention, one or more other substances and/or treatments. Such conjoint tent may be achieved by way of the simultaneous, sequential or separate administration of the individual components of the treatment. According to this aspect of the invention there is provided a pharmaceutical product comprising a compound of the formula (I), or a pharmaceutically acceptable salt, solvate, solvate of such a salt or a prodrug thereof, as defined hereinbefore and an additional IBAT inhibitory substance as defined hereinbefore and an additional hypolipidaemic agent for the conjoint treatment of hyperlipidaemia.

In another aspect of the invention, the compound of formula (I), or a pharmaceutically acceptable salt, solvate, solvate of such a salt or a prodrug thereof, may be administered in association with an HMG Co-A reductase inhibitor, or pharmaceutically acceptable salts, solvates, solvates of such salts or prodrugs thereof. Suitable HMG Co-A reductase inhibitors, pharmaceutically acceptable salts, solvates, solvates of such salts or prodrugs thereof are statins well known in the art. Particular statins are fluvastatin, lovastatin, pravastatin, simvastatin, atorvastatin, cerivastatin, bervastatin, dalvastatin, mevastatin and (E)-7-[4-(4-fluorophenyl)-6-isopropyl-2-[methyl(methylsulphonyl) amino]pyrimidin-5-yl](3R,5S)-3,5-dihydroxyhept-6-enoic acid (rosuvastatin), or a pharmaceutically acceptable salt, solvate, solvate of such a salt or a plug thereof. A particular statin is atorvastatin, or a pharmaceutically acceptable salt, solvate, solvate of such a salt or a prodrug thereof. A more particular statin is atorvastatin calcium salt. A further particular statin is (E)-7-[4-(4-fluorophenyl)-6-isopropyl-2-[methyl(methylsulphonyl)amino]pyrimidin-5-yl](3R,5S)-3,5-dihydroxyhept-6-enoic acid (rosuvastatin), or a pharmaceutically acceptable salt, solvate, solvate of such a salt or a prodrug thereof. A preferable particular statin is rosuvastatin calcium salt.

In an additional aspect of the invention, the compound of formula (I), or a pharmaceutically acceptable salt, solvate, solvate of such a salt or a prodrug thereof may be administered in association with an HMG Co-A reductase inhibitor, or a pharmaceutically acceptable salt, solvate, solvate of such a salt or a prodrug thereof, and/or a bile acid binder thereby avoiding a possible risk of excess of bile acids in colon caused by the inhibition of the ileal bile acid transport system. An excess of bile acids in the visceral contents may cause diarrhoea. Thus, the present invention also provides a treatment of a possible side effect such as diarrhoea in patients during therapy comprising the compound of formula (I), or a pharmaceutically acceptable salt, solvate, solvate of such a salt or a prodrug thereof.

An HMG CoA-reductase inhibitor, or a pharmaceutically acceptable salt, solvate, solvate of such a salt or a prodrug thereof will by its action decrease the endogenous cholesterol available for the bile acid synthesis and have an additive effect in combination with the compound of formula (I), or a pharmaceutically acceptable salt, solvate, solvate of such a salt or a prodrug thereof on lipid lowering.

Suitable bile acid binders for such a combination therapy are resins, such as cholestyramine and cholestipol. One advantage is that the dose of bile acid binder might be kept lower than the therapeutic dose for treatment of cholesterolaemia in single treatment comprising solely a bile acid binder. By a low dose of bile acid binder any possible side effects caused by poor tolerance of the patient to the therapeutic dose could also be avoided.

Therefore in an additional feature of the invention, there is provided a method for producing an IBAT inhibitory effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of an HMG Co-A reductase inhibitor, or a pharmaceutically acceptable salt, solvate, solvate of such a salt or a prodrug thereof.

Therefore in an additional feature of the invention, there is provided a method for producing an IBAT inhibitory effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with a bile acid binder.

Therefore in an additional feature of the invention, there is provided a method for producing an IBAT inhibitory effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of an HMG Co-A reductase inhibitor, or a pharmaceutically acceptable salt, solvate, solvate of such a salt or a prodrug thereof, in simultaneous, sequential or separate administration with a bile acid binder.

Therefore in an additional feature of the invention, there is provided a method of treating hyperlipidemic conditions in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of an HMG Co-A reductase inhibitor, or a pharmaceutically acceptable salt, solvate, solvate of such a salt or a prodrug thereof.

Therefore in an additional feature of the invention, there is provided a method of treating hyperlipidemic conditions in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of a bile acid binder.

Therefore in an additional feature of the invention, there is provided a method of treating hyperlipidemic conditions in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of an HMG Co-A reductase inhibitor, or a pharmaceutically acceptable salt, solvate, solvate of such a salt or a prodrug thereof, in simultaneous, sequential or separate administration with a bile acid binder.

According to a further aspect of the invention there is provided a pharmaceutical composition which comprises a compound of formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof, in association with a pharmaceutically acceptable diluent or carrier.

According to a further aspect of the invention there is provided a pharmaceutical composition which comprises a compound of formula (I), or a pharmaceutically acceptable salt, solvate, solvate of such a salt or a prodrug thereof, and a bile acid binder, in association with a pharmaceutically acceptable diluent or carrier.

According to a further aspect of the invention there is provided a pharmaceutical composition which comprises a compound of formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof, and a bile acid binder in association with a pharmaceutically acceptable diluent or carrier.

According to a further aspect of the present invention there is provided a kit comprising a compound of formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof.

According to a further aspect of the present invention there is provided a kit comprising a compound of formula (I), or a pharmaceutically acceptable salt, solvate, solvate of such a salt or a prodrug thereof, and a bile acid binder.

According to a further aspect of the present invention there is provided a kit comprising a compound of formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof and a bile acid binder.

According to a further aspect of the present invention there is provided a kit comprising:

a) a compound of formula (I), or a pharmaceutically acceptable salt, solvate, solvate of such a salt or a prodrug thereof, in a first unit dosage form;

b) an HMG Co-A reductase inhibitor, or a pharmaceutically acceptable salt, solvate, solvate of such a salt or a prodrug thereof; in a second unit dosage form; and c) container means for containing said first and second dosage forms.

According to a further aspect of the present invention there is provided a kit comprising:

a) a compound of formula (I), or a pharmaceutically acceptable salt, solvate, solvate of such a salt or a prodrug thereof, in a first unit dosage form;

b) a bile acid binder; in a second unit dosage form; and c) container means for containing said first and second dosage forms.

According to a further aspect of the present invention there is provided a kit comprising:

a) a compound of formula (I), or a pharmaceutically acceptable salt, solvate, solvate of such a salt or a prodrug thereof, in a first unit dosage form;

b) an, HMG Co-A reductase inhibitor, or a pharmaceutically acceptable salt, solvate, solvate of such a salt or a prodrug thereof; in a second unit dosage form;
c) a bile acid binder, in a third unit dosage form; and
d) container means for containing said first, second and third dosage forms.

According to a further aspect of the present invention there is provided a kit comprising:
a) a compound of formula (I), or a pharmaceutically acceptable salt, solvate, solvate of such a salt or a prodrug thereof, together with a pharmaceutically acceptable diluent or carrier, in a first unit dosage form;
b) an HMG Co-A reductase inhibitor, or a pharmaceutically acceptable salt, solvate, solvate of such a salt or a prodrug thereof, in a second unit dosage form; and
c) container means for containing said first and second dosage forms.

According to a Per aspect of the present invention there is provided a kit comprising:
a) a compound of formula (I), or a pharmaceutically acceptable salt, solvate, solvate of such a salt or a prodrug thereof, together with a pharmaceutically acceptable diluent or carrier, in a first unit dosage form;
b) a bile acid binder, in a second unit dosage form; and
c) container means for containing said first and second dosage forms.

According to a further aspect of the present invention there is provided a kit comprising:
a) a compound of formula (I), or a pharmaceutically acceptable salt, solvate, solvate of such a salt or a prodrug thereof, together with a pharmaceutically acceptable diluent or carrier, in a first unit dosage form;
b) an HMG Co-A reductase inhibitor, or a pharmaceutically acceptable salt, solvate, solvate of such a salt or a prodrug thereof, in a second unit dosage form; and
c) a bile acid binder; in a third unit dosage form; and
d) container means for containing said first, second and third dosage forms.

According to another feature of the invention there is provided the use of a compound of the formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof, in the manufacture of a medicament for use in the production of an IBAT inhibitory effect in a warm-blooded animal, such as man.

According to another feature of the invention there is provided the use of a compound of the formula (I), or a pharmaceutically acceptable salt, solvate, solvate of such a salt or a prodrug thereof, and a bile acid binder, in the manufacture of a medicament for use in the production of an IBAT inhibitory effect in a warm-blooded animal, such as man.

According to another feature of the invention there is provided the use of a compound of the formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof, and a bile acid binder, in the manufacture of a medicament for use in the production of an IBAT inhibitory effect in a warm-blooded animal, such as man.

According to another feature of the invention there is provided the use of a compound of the formula (I), or a pharmaceutically acceptable salt, solvate, solvate of such a salt or a prodrug thereof, an HMG Co-A reductase inhibitor, or a pharmaceutically acceptable salt, solvate, solvate of such a salt or a prodrug thereof, in the manufacture of a medicament for use in the treatment of hyperlipidaemic conditions in a warm-blooded animal, such as man.

According to another feature of the invention there is provided the use of a compound of the formula (I), or a pharmaceutically acceptable salt, solvate, solvate of such a salt or a prodrug thereof, a bile acid binder, in the manufacture of a medicament for use in the treatment of hyperlipidaemic conditions in a warm-blooded animal, such as man.

According to another feature of the invention there is provided the use of a compound of the formula (I), or a pharmaceutically acceptable salt, solvate, solvate of such a salt or a prodrug thereof, an HMG Co-A reductase inhibitor, or a pharmaceutically acceptable salt, solvate, solvate of such a salt or a prodrug thereof, and a bile acid binder, in the manufacture of a medicament for use in the treatment of hyperlipidaemic conditions in a warm-blooded animal, such as man.

According to a further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of an HMG Co-A reductase inhibitor, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

According to a further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of a bile acid binder, optionally together with a pharmaceutically acceptable diluent or carrier to a warm-blooded animal, such as man in need of such therapeutic treatment.

According to a further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of an HMG Co-A reductase inhibitor, or a pharmaceutically acceptable salt, solvate, solvate of such a salt or a prodrug thereof, optionally together with a pharmaceutically acceptable excipient, with the simultaneous, sequential or separate administration of an effective amount of a bile acid binder, optionally together with a pharmaceutically acceptable diluent or carrier to a warm-blooded animal, such as man in need of such therapeutic treatment.

According to an additional further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration one or more of the following agents selected from:
a CETP (cholesteryl ester transfer protein) inhibitor, for example those referenced and described in WO 00/38725 page 7 line 22—page 10, line 17 which are incorporated herein by reference;,
a cholesterol absorption antagonist for example azetidinones such as SCH 58235 and those described in U.S. Pat. No. 5,767,115 which are incorporated herein by reference;
a MTP (microsomal transfer protein) inhibitor for example those described in Science, 282, 751–54, 1998 which are incorporated herein by reference;
a fabric acid derivative; for example clofibrate, gemfibrozil, fenofibrate, ciprofibrate and bezafibrate;
a nicotinic acid derivative, for example, nicotinic acid (niacin), acipimox and niceritrol;
a phytosterol compound for example stanols;
probucol;
an anti-obesity compound for example orlistat (EP 129,748) and sibutramine (GB 2,184,122 and U.S. Pat. No. 4,929,629);
an antihypertensive compound for example an angiotensin converting enzyme (ACE) inhibitor, an angiotensin II receptor antagonist, an andrenergic blocker, an alpha andrenergic blocker, a beta andrenergic blocker, a mixed alpha/beta andrenergic blocker, an andrenergic stimulant, calcium channel blocker, a diuretic or a vasodilator,
insulin;
sulphonylureas including glibenclamide, tolbutamide;
metformin; and/or
acarbose;

or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

Particular ACE inhibitors or pharmaceutically acceptable salts, solvates, solvate of such salts or a prodrugs thereof, including active metabolites, which can be used in combination with a compound of formula (I) include but are not limited to, the following compounds: alacepril, alatriopril, altiopril calcium, ancovenin, benazepril, benazepril hydrochloride, benazeprilat, benzoylcaptopril, captopril, captopril-cysteine, captopril-glutathione, ceranapril, ceranopril, ceronapril, cilazapril, cilazaprilat, delapril, delapril-acid, enalapril, enalaprilat, enapril, epicaptopril, foroxyniithine, fosfenopril, fosenopril, fosenopril sodium, fosinopril, fosinopril sodium, fosinoprilat, fosinoprilic acid, glycopril, hemorphin-4, idrapril, imidapril, indolapril, indolaprilat, libenzapril, lisinopril, lyciumin A, lyciumin B, mixanpril, moexipril, moexiprilat, moveltipril, muracein A, muracein B, muracein C, pentopril, perindopril, perindoprilat, pivalopril, pivopril, quinapril, quinapril hydrochloride, quinaprilat, ramipril, ramiprilat, spirapri, spirapril hydrochloride, spiraprilat, spiropril, spiropril hydrochloride, temocapril, temocapril hydrochloride, teprotide, trandolapril, trandolaprilat, utibapril, zabicipril, zabiciprilat, zofenopril and zofenoprilat. Preferred ACE inhibitors for use in the present invention are ramipril, ramiprilat, lisinopril, enalapril and enalaprilat. More preferred ACE inhibitors for uses in the present invention are ramipril and ramiprilat.

Preferred angiotensin II antagonists, pharmaceutically acceptable salts, solvates, solvate of such salts or a prodrugs thereof for use in combination with a compound of formula (I) include, but are not limited to, compounds: candesartan, candesartan cilexetil, losartan, valsartan, irbesartan, tasosartan, telmisartan and eprosartan. Particularly preferred angiotensin II antagonists or pharmaceutically acceptable derivatives thereof for use in the present invention are candesartan and candesartan cilexetil.

In another aspect of the invention, the compound of formula (I), or a pharmaceutically acceptable salt, solvate, solvate of such a salt or a prodrug thereof, may be administered in association with a PPAR alpha and/or gamma agonist, or pharmaceutically acceptable salts, solvates, solvates of such salts or prodrugs thereof. Suitable PPAR alpha and/or gamma agonists, pharmaceutically acceptable salts, solvates, solvates of such salts or prodrugs thereof are well known in the art. These include the compounds described in WO 01/12187, WO 01/12612, WO 99/62870, WO 99/62872, WO 99/62871, WO 98/57941, WO 01/40170, J Med Chem, 1996, 39, 665, Expert Opinion on Therapeutic Patents, 10 (5), 623–634 (in particular the compounds described in the patent applications listed on page 634) and J Med Chem, 2000, 43, 527 which are all incorporated herein by reference. Particularly a PPAR alpha and/or gamma agonist refers to WY-14643, clofibrate, fenofibrate, bezafibrate, GW 9578, troglitazone, pioglitazone, rosiglitazone, eglitazone, proglitazone, BRL-49634, KRP-297, JTT-501, SB 213068, GW 1929, GW 7845, GW. 0207, L-796449, L-165041 and GW 2433. Particularly a PPAR alpha and/or gamma agonist refers to (S)-2-ethoxy-3-[4-(2-{4-methanesulphonyloxyphenyl}ethoxy)phenyl]propanoic acid and pharmaceutically acceptable salts thereof. Additional suitable PPAR alpha and/or gamma agonists are NN622/Ragaglitazar and BMS 298585.

Therefore in an additional feature of the invention, there is provided a method for producing an IBAT inhibitory effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of a PPAR alpha and/or gamma agonist, or a pharmaceutically acceptable salt, solvate, solvate of such a salt or a prodrug thereof.

Therefore in an additional feature of the invention, there is provided a method of treating hyperlipidemic conditions in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of a PPAR alpha and/or gamma agonist, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt, solvate, solvate of such a salt or a prodrug thereof, and a PPAR alpha and/or gamma agonist, or a pharmaceutically acceptable salt, solvate, solvate of such a salt or a prodrug thereof, in association with a pharmaceutically acceptable diluent or carrier.

According to a further aspect of the present invention there is provided a kit comprising a compound of formula (I), or a pharmaceutically acceptable salt, solvate, solvate of such a salt or a prodrug thereof, and a PPAR alpha and/or gamma agonist, or a pharmaceutically acceptable salt, solvate, solvate of such a salt or a prodrug thereof.

According to a further aspect of the present invention there is provided a kit comprising:

a) a compound of formula (I), or a pharmaceutically acceptable salt, solvate, solvate of such a salt or a prodrug thereof, in a first unit dosage form;
b) a PPAR alpha and/or gamma agonist, or a pharmaceutically acceptable salt, solvate, solvate of such a salt or a prodrug thereof; in a second unit dosage form; and
c) container means for containing said first and second dosage forms.

According to a further aspect of the present invention there is provided a kit comprising:
a) a compound of formula (I), or a pharmaceutically acceptable salt, solvate, solvate of such a salt or a prodrug thereof, together with a pharmaceutically acceptable diluent or carrier, in a first unit dosage form;
b) a PPAR alpha and/or gamma agonist, or a pharmaceutically acceptable salt, solvate, solvate of such a salt or a prodrug thereof, in a second unit dosage form; and
c) container means for containing said first and second dosage forms.

According to another feature of the invention there is provided the use of a compound of the formula (I), or a pharmaceutically acceptable salt, solvate, solvate of such a salt or a prodrug thereof, and a PPAR alpha and/or gamma agonist, or a pharmaceutically acceptable salt, solvate, solvate of such a salt or a prodrug thereof, in the manufacture of a medicament for use in the production of an IBAT inhibitory effect in a warm-blooded animal, such as man.

According to another feature of the invention there is provided the use of a compound of the formula (I), or a pharmaceutically acceptable salt, solvate, solvate of such a salt or a prodrug thereof, a PPAR alpha and/or gamma agonist, or a pharmaceutically acceptable salt, solvate, solvate of such a salt or a prodrug thereof, in the manufacture of a medicament for use in the treatment of hyperlipidaemic conditions in a warn-blooded animal, such as man.

According to a further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of a PPAR alpha and/or gamma agonist, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

In addition to their use in therapeutic medicine, the compounds of formula (I), or a pharmaceutically acceptable salt, solvate, solvate of such a salt or a prodrug thereof, are also useful as pharmacological tools in the development and standardisation of in vitro and in vivo test systems for the evaluation of the effects of inhibitors of IBAT in laboratory animals such as cats, dogs, rabbits, monkeys, rats and mice, as part of the search for new therapeutic agents.

Many of the intermediates described herein are novel and are thus provided as a further feature of the invention.

In the above other pharmaceutical composition, process, method, use and medicament manufacture features, the alternative and particular embodiments of the compounds of the invention described herein also apply.

EXAMPLES

The invention will now be illustrated in the following non limiting examples, in which standard techniques known to the skilled chemist and techniques analogous to those described in these examples may be used where appropriate, and in which, unless otherwise stated:

(i) evaporations were carried out by rotary evaporation in vacuo and work up procedures were carried out after removal of residual solids such as drying agents by filtration;

(ii) all reactions were carried out under an inert atmosphere at ambient temperature, typically in the range 18–25° C., with solvents of HPLC grade under anhydrous conditions, unless otherwise stated;

(iii) column chromatography (by the flash procedure) was performed on Silica gel 40–63 μm (Merck);

(iv) yields are given for illustration only and are not necessarily the maximum attainable;

(v) the structures of the end products of the formula (I) were generally confirmed by nuclear (generally proton) magnetic resonance (NMR) and mass spectral techniques; magnetic resonance chemical shift values were measured in deuterated $CD_3OD$ (unless otherwise stated) on the delta scale (ppm downfield from tetramethylsilane); proton data is quoted unless otherwise stated; spectra were recorded on a Varian Mercury-300 MHz, Varian Unity plus-400 MHz, Varian Unity plus-600 MHz or on Varian Inova-500 MHz spectrometer, and peak multiplicities are shown as follows: s, singlet; d, doublet; dd, double doublet; t, triplet; tt, triple triplet; q, quartet; tq, triple quartet; m, multiplet; br, broad; LCMS were recorded on a Waters ZMD, LC column xTerra MS $C_8$(Waters), detection with a HP 1100 MS-detector diode array equipped; mass spectra (MS) (loop) were recorded on VG Platform II (Fisons Instruments) with a HP-1100 MS-detector diode array equipped; unless otherwise stated the mass ion quoted is $(MH^+)$;

(vi) unless further details are specified in the text, analytical high performance liquid chromatography (HPLC) was performed on Prep LC 2000 (Waters), Kromasil $C_8$, 7 μm, (Akzo Nobel); MeCN and de-ionised water 100 mM ammonium acetate as mobile phases, with suitable composition;

(vii) intermediates were not generally fully characterised and purity was assessed by thin layer chromatography (TLC), HPLC, infra-red (IR), MS or NMR analysis;

(viii) where solutions were dried sodium sulphate was the drying agent;

(ix) where an "ISOLUTE" column is referred to, this means a column containing 2 g of silica, the silica being contained in a 6 ml disposable syringe and supported by a porous disc of 54 Å pore size, obtained from International Sorbent Technology under the name "ISOLUTE"; "ISOLUTE" is a registered trade mark;

(x) the following abbreviations may be used hereinbefore or hereinafter:—

DCM dichloromethane;

DMF N,N-dimethylformamide;

TBTU o-Benzotriazol-1-yl-N,N,N',N'-tetramethyluronium tetrafluoroborate;

EtOAc ethyl acetate;

MeCN acetonitrile;

TFA trifluoroacetic acid;

HATU o-(7-azabenzotriazol-1-yl)-N,N,N',N'-tetramethyluronium hexafluoro-phosphate; and DIPEA di-isopropylethyiamine.

Example 1

1,1-Dioxo-3,3-dibutyl-5-phenyl-7-methylthio-8-(N-{(R)-α-[N-(2-(S)-3-(R)-4-(R)-5-(R)-2,3,4,5,6-pentahydroxyhexyl)carbamoyl]benzyl}carbamoylmethoxy)-2,3,4,5-tetrahydro-1,2,5-benzothiadiazenine A solution of 1,1-dioxo-3,3-dibutyl-5-phenyl-7-methylthio-8-[N—((R)-α-carboxybenzyl)carbamoylmethoxyl]-2,3,4,5-tetrahydro-1,2,5-benzothiadiazepine (Method 1; 0.055 g, 0.086 mmol), D-glucitol, 1-amino-1-deoxy-(0.017 g, 0.094 mmol) and N-methylmorpholine (0.028 ml, 0.254 mmol) in DMF (4 ml) was stirred for 10 min, after which TBTU (0.033 g, 0.103 mmol) was added. After 18 h the solution was diluted with toluene and then concentrated. The residue was purified by preparative HPLC using a gradient of 40–60% MeCN in 0.1M ammonium acetate buffer as eluent The title compound was obtained in 0.041 g (59%) as a white solid. NMR (400 MHz, DMSO-$d_6$): 0.60–0.85 (6H, m), 0.85–1.65 (12H, m), 2.10 (3H, s), 2.95–3.05 (1H, m), 3.20–3.70 (17H (7CH+H2O), m), 3.85 (2H, bs), 4.20–4.45 (4H, m), 4.60–4.80 (3H, m), 5.55 (1H, d), 6.60 (1H, s), 6.90–7.50 (12H, m), 8.30–8.55 (2H, m); m/z 803.3429.

Example 2

1,1-Dioxo-3,3-dibutyl-5-phenyl-7-methylthio-8-(N-{(R)-α-[N-(2-(S)-3-(R)-4-(R)-5-(R)-2,3,4,5,6-pentahydroxyhexyl)carbamoyl]-4-hydroxybenzyl}carbamoylmethoxy)-2,3,4,5-tetrahydro-1,2,5-benzothiadiazepine 1,1-Dioxo-3,3-dibutyl-5-phenyl-7-methylthio-8-[N-((R)-α-carboxy-4-hydroxybenzyl) carbamoylmethoxy]-2,3,4,5-tetrahydro-1,2,5-benzothiadiazepine (Method 5; 45.5 mg, 0.070 mmol) was dissolved in 3 ml DMF. N-Methylmorpholine (16 μl, 14 mmol) and D-glucamine (16 mg, 0.084 mmol) were added and the mixture was stirred for 20 min. TBTU (27 mg, 0.084 mmol) was added and the reaction mixture was stirred overnight. To obtain complete transformation of the starting material, D-glucamine (13.5 mg, 0.079 mmol), N-methylmorpholine (8 μl, 0.070 mmol), catalytic amount of tetrabutylammonium bromide and TBTU (3×5 mg in portions, 0.04 mmol) were added successively. The reaction mixture was concentrated and purified using preparative HPLC on a C8 column (50×250 mm) with a gradient (20/80 to 50/50) of MeCN/0.1M ammonium acetate buffer as eluent. The product fraction was concentrated to remove the MeCN and then lyophilized to yield the title compound in 31 mg (53% yield). NMR (400 MHz): 0.8 (t, 6H), 1.0–1.2 (m, 6H), 1.25–1.4 (m, 2H), 1.4–1.5 (m, 2H), 1.55–1.7 (m, 2H), 2.1 (s, 3H), 3.15–3.25 (m, 2H), 3.45–3.7 (m, 5H), 3.73 (dd, 1H), 3.8–3.85 (m, 1H), 3.95 (brs, 2H), 4.6 (ABq, 2H), 5.3 (s, 1H), 6.6 (s, 1H), 6.75 (d, 2H), 7.05 (t, 1H) 7.15–7.4 (m, 7H); m/z: 819.

Examples 3 and 4

1,1-Dioxo-3,3-dibutyl-5-phenyl-7-methylthio-8-[N-((R/S)-α-{N-[1-(R)-2-(S)-1-hydroxy-1-(3,4-dihydroxyphenyl)prop-2-yl]carbamoyl}benzyl)carbamoylmethoxy]-2,3.4,5-tetrahydro-1,2,5-benzothiadiazepine enantiomer 1

1,1-Dioxo-3,3-dibutyl-5-phenyl-7-methylthio-8-[N-((R/S)-α-{N-[1-(R)-2-(S)-1-hydroxy-1-(3,4-dihydroxyphenyl)prop-2-yl]carbamoyl}benzyl)carbamoylmethoxy]-2,3,4,5-tetrahydro-1,2,5-benzothiadiazepine enantiomer 2

1,1-Dioxo-3,3-dibutyl-5-phenyl-7-methylthio-8-[N-((R)-α-carboxybenzyl) carbamoylmethoxy]-2,3,4,5-tetrahydro-1,2,5-benzothiadiazepine (Method 1; 50 mg, 0.078 mmol) and 4-[(1R,2S)-2-amino-1-hydroxypropyl]benzene-1,2-diol (17.9 mg, 0.098 mmol) were dissolved in DCM (1 ml), DMF (2 ml). N-Methylmorpholine (17.2 μl, 0.156 mmol) and TBTU (45 mg, 0.14 mmol) were added. The reaction mixture was stirred over night and then evaporated under reduced pressure. Proton NMR showed a mixture of two diastereomers due to epimerisation in the phenylglycinresidue. The two diastereomers was separated by preparative HPLC using an acetonitrile/ammonium acetate buffer gradient (5/95 to 100/0) as eluent. The diastereomer that eluted first gave 7 mg (11%) after lyophilisation. NMR (500 MHz): 0.81 (brt, 6H), 1.0–1.26 (m, 9H), 1.26–1.41 (m, 2H), 1.42–1.53 (m, 2H), 1.57–1.7 (m, 2H), 2.11 (s, 3H), 3.85–4.2 (m, 3H), 4.33 (d, 1H), 4.65 (ABq, 2H), 5.47 (s, 1H), 6.53 (dd, 1H), 6.57–6.63 (m, 2H), 6.73 (d, 1H), 7.07 (brt, 1H), 7.11–7.17 (m, 2H), 7.18–7.38 (m, 8H); m/z 803.9 (M–H)⁻. The diastereomer eluted second gave 15 mg (24%) after lyophilisation. NMR (500 MHz): 0.81 (brt, 6H), 1.0–1.25 (m, 9H), 1.25–1.4 (m, 2H), 1.42–1.52 (m, 2H), 1.57–1.7 (m, 2H), 2.12 (s, 3H), 3.8–4.13 (m, 3H), 4.56–4.74 (m, 3H), 5.47 (s, 1H), 6.61 (brs, 1H), 6.67–6.73 (m, 2H), 6.83 (s, 1H), 7.07 (brt, 1H), 7.15–7.40 (m, 10H); m/z 803.9 (M–)⁻.

Example 5

1,1-Dioxo-3,3-dibutyl-5-phenyl-7-methylthio-8-{N-[(R)-α-(N-{2-(S)-[N-(carbamoylmethyl) carbamoyl]pyrrolidin-1-ylcarbonylmethyl}carbamoyl)benzyl]carbamoylmethoxy}-2,3,4,5-tetrahydro-1,2,5-benzothiadiazepine 1,1-Dioxo-3,3-dibutyl-5-phenyl-7-methylthio-8-[N-((R)-α-carboxybenzyl) carbamoylmethoxy]-2,3,4,5-tetrahydro-1,2,5-benzothiadiazepine (Method 1; 46 mg, 0.070 mmol) was dissolved in DMF (2 ml). (2S)-1-(aminoacetyl)-N-(carbamoylmethyl)pyrrolidine-2-carboxamide (25 mg, 0.094 mmol) and N-methylmorpholine (16 μl, 0.145 mmol) were added. The solution became cloudy and DMF (1 ml) was added. TBTU (21 mg, 0.084 mmol) was added in two portions over 10 minutes and the mixture was stirred for 1.5 hours. Formic acid (2 drops) was added after 2 hours. The mixture was purified using preparative HPLC on a C8 column (50×250 mm). A step gradient from 20–60% MeCN in 0.1M ammonium acetate buffer was used as eluent. The product fraction was concentrated and lyophilised to yield 22 mg (37%). NMR (400 MHz, CD₃OD): 0.79 (t, 6H), 0.98–1.24 (m, 6H), 1.24–1.4 (m, 2H), 1.46 (brt, 2H), 1.55–1.7 (m, 2H),1.85–2.12 (m, 6H), 2.12–2.24 (m, 1H), 3.4–3.66(m, 2H), 3.7–4.15 (m, 6H), 4.31–4.37 (m, 1H), 4.63 (ABq, 2H), 5.61 (s, 1H), 6.58 (s, 1H), 7.04 (t, 1H), 7.20 (brd, 2H), 7.24–7.38 (m, 6H), 7.46 (brd, 2H).

Example 6

1,1-Dioxo-3.3-dibutyl-5-phenyl-7-methylthio-8-[N-((R)-α-{N-[2-(3,4,5-trihydroxyphenyl)ethyl]carbamoyl}benzyl)carbamoylmethoxy]-2,3,4,5-tetrahydro-1,2,5-benzothiadiazepine 1,1-Dioxo-3,3-dibutyl-5-phenyl-7-methylthio-8-[N-((R)-α-carboxybenzyl) carbamoylmethoxy]-2,3,4,5-tetrahydro-1,2,5-benzothiadiazepine (Method 1; 60 mg, 0.094 mmol), 5-(2-aminoethyl)benzene-1,2,3-triol (25 mg, 0.12 mmol)- and N-methylmorpholine (21 µl, 0.188 mmol) were dissolved in DMF (2 ml). TBTU (38 mg, 0.12 mmol) was added and the mixture was stirred for 45 minutes. The product was purified by preparative HPLC using a MeCN/ammonium acetate buffer gradient (5/95 to 100/0) as eluent to give the title compound 37 mg (50%). NMR (400 Mz, CD$_3$OD): 0.79 (t, 6H), 0.95–1.24 (m, 6H), 1.24–1.39 (m, 2H), 1.45 (brt, 2H), 1.54–1.69 (m, 2H), 2.09 (s, 3H), 2.53 (t, 2H), 3.35 (t, 2H), 3.75–4.12 (m, 2H), 4.64 (ABq, 2H), 5.44 (s, 1H), 6.16 (s, 2H), 6.58 (s, 1H), 7.04 (brt; 1H), 7.11–7.45 (m, 10H).

Example 7

1,1-Dioxo-3,3-dibutyl-5-phenyl-7-methylthio-8-(N-{(R)-α-[N-(2-(R)-3-(S)-4-(S)-5-(R)-3,4,5,6-tetrahydroxytetrahydropyran-2-ylmethyl)carbamoyl]benzyl}carbamoylmethoxy)-2,3,4,5-tetrahydro-1,2,5-benzothiadiazepine 1,1-Dioxo-3,3-dibutyl-5-phenyl-7-methylthio-8-[N-((R)-α-carboxybenzyl) carbamoylmethoxyl]-2,3,4,5-tetrahydro-1,2,5-benzothiadiazepine (Method 1; 56 mg, 0.088 mmol), 3-(R)-4-(S)-5-(S)-6-(R)-2,3,4,5-tetrahydroxy-6-(aminomethyl) tetrahydropyran (25.4 mg, 0.12 mmol) and N-methylmorpholine (19 µl, 0.175 mmol) were dissolved in DMF (2 ml) and water (10 drops). TBTU (34 mg, 0.105 mmol) was added and the mixture was stirred for 2 hours. More TBTU (22 mg) and 3-(R)-4-(S)-5-(S)-6-(R)-2,3,4,5-tetrahydroxy-6-(aminomethyl)tetrahydropyran (5 mg) were added and stirred for a short period. The product was purified by preparative HPLC using a MeCN/ammonium acetate buffer gradient (5/95 to 100/0) as eluent to give the title compound 39 mg (56%). M/z 799.55 (M–H)$^-$.

Preparation of Starting Materials

The starting materials for the Examples above are either commercially available or are readily prepared by standard methods from known materials. For example, the following reactions are an illustration, but not a limitation, of some of the starting materials used in the above reactions.

Method 1

1,1-Dioxo-3,3-dibutyl-5-phenyl-7-methylthio-8-[N-((R)-α-carboxybenzyl) carbamoylmethoxy]-2,3,4,5-tetrahydro-1,2,5-benzothiadiazepine 1,1-Dioxo-3,3-dibutyl-5-phenyl-7-methylthio-8-{N-[(R)-α-(t-butoxycarbonyl)benzyl]carbamoylmethoxy}-2,3,4,5-tetrahydro-1,2,5-benzothiadiazepine (Method 2; 762 mg, 1.09 mmol) was dissolved in a mixture of TFA (6.65 ml) and triethylsilane (0.350 ml). The reaction mixture was stirred for one hour and then evaporated under reduced pressure to give the title compound in a quantitative yield (714 mg). NMR (500 MHz): 0.8 (brt, 6H), 0.96–1.25 (m, 6H), 1.25–1.4 (m, 2M), 1.42–1.51 (m, 2H), 1.57–1.69 (m, 2H), 2.11 (s, 3H), 3.8–4.15 (m, 2H), 4.66 (ABq, 2H), 5.49–5.53 (m, 1H), 6.61 (s, 1H), 7.06 (t, 1H), 7.18–7.26 (m, 2H), 7.28–7.45 (m, 8H), 8.35 (d, NH); m/z 640.2.

Method 2

1,1-Dioxo-3,3-dibutyl-5-phenyl-7-methylthio-8-{N—[(R)-α-(t-butoxycarbonyl)benzyl]carbamoylmethoxy}-2,3,4,5-tetrahydro-1,2,5-benzothiadiazepine 1,1-Dioxo-3,3-dibutyl-5-phenyl-7-methylthio-8-carboxymethoxy-2,3,4,5-tetrahydro-1,2,5-benzothiadiazepine (Method 3; 627 mg, 1.24 mmol) was dissolved in DCM (25 ml), tert-butyl (2R)-amino(phenyl)acetate (308 mg, 1.48 mmol, 2,6-dimethylpyridine (288 µl, 2.47 mmol) and TBTU (477 mg, 1.48 mmol) were added. The mixture was stirred for 3.5 hours. The reaction mixture was evaporated under reduced pressure. The product was purified using an Isolute column (10 g, silica). The product was eluted with a stepwise gradient using DCM:EtOAc 100:0 then 95:5. Approximately 694 mg pure compound was collected An additional fraction was purified a second time using an Isolute column (10 g, silica). The product was eluted with a stepwise gradient using DCM:EtOAc 100:0, 95:5 then 90:10. The pure fraction was added to the first fraction yielding 787 mg (91%) of the title compound. NMR (400 MHz, CDCl$_3$) 0.78 (t, 6H), 0.92–1.12 (m, 4H), 1.12–1.46 (m, 6H), 1.54 (s, 9H), 1.58–1.72 (m, 2H:), 2.14 (s, 3H), 3.8–4.05 (m, 2H), 4.32 (brs, NH), 4.56 (ABq, 2H), 5.56 (d, 1H), 6.56 (s, 1H), 7.04 (t, 1H), 7.10 (brd, 2H) 7.24–7.42 (m, 8H), 7.84 (d, NH); m/z 694.7 (M–H)$^-$.

Method 3

1,1-Dioxo-3,3-dibutyl-5-phenyl-7-methylthio-8-carboxymethoxy-2,3,4,5-tetrahydro-1,2,5-benzothiadiazepine To a solution of 1,1-dioxo-3,3-dibutyl-5-phenyl-7-methylthio-8-ethoxycarbonyl-methoxy-2,3,4,5-benzothiadiazepine (Method 4; 0.024 g, 4.49*10$^{-5}$ mol) in EtOH (3 ml) was added NaOH (0.007 g, 1.80*10$^{-4}$ mol) and the mixture was stirred over night The solvent was removed under reduced pressure and the residue was purified by preparative HPLC using an MeCN/ammonium acetate buffer as eluent and freeze-dried The title compound was obtained in 0.021 g (92%) as a white solid. NMR (400 MHz, CD$_3$OD) 0.70–0.85 (m, 6H), 1.00–1.70 (m, 12H), 2.10 (s, 3H), 3.90 (brs, 2H), 4.55 (s, 2H), 6.60 (s, 1H), 6.90–7.35 (m, 6H).

Method 4

1,1-Dioxo-3,3-dibutyl-5-phenyl-7-methylthio-8-ethoxycarbonylmethoxy-2,3,4,5-tetrahydro-1,2,5-benzothiadiazepine To a suspension of 1,1-dioxo-3,3-dibutyl-5-phenyl-7-bromo-8-methoxy-2,3,4,5-tetrahydro-1,2,5-benzothiadiazepine (prepared according to WO 98/38182; 0.218 g, 5.65*10$^{-4}$ mol) in DMF (5 ml) was added NaSMe (0.210 g, 2.83 mmol, 95%), and the mixture was stirred for 5 hours at 120° C. The solvent was removed under reduced pressure and the residue was partitioned between EtOAc and 0.5 M HCl. The aqueous layer was extracted twice more with EtOAc and the combined organic extracts were dried (MgSO$_4$) and concentrated The residue was dissolved in MeCN (7 ml) and ethyl bromoacetate (0.063 ml, 5.65*10$^{-4}$ mol), tetrabutylammonium bromide (0.018 g, 5.65*10$^{-5}$ mol) and sodium carbonate (0.250 g, 2.36 mmol) were added. The mixture was stirred over night at 80° C. The solvent was removed under reduced pressure and the residue was partitioned between EtOAc and 0.5 M HCl. The organic layer was washed with brine, dried (MgSO$_4$) and concentrated Flash chromatography on silica gel (Hex:EtOAc-6:1) gave the title compound as a colourless oil 0.024 g (8%). NMR (400 MHz, CDCl$_3$) 0.70–0.85 (m, 6H), 0.90–1.70 (m, 15H), 2.10 (s, 3H), 3.90 (bs, 2H), 4,20 (bs, 1H), 4.25 (q, 2H), 4.65 (s, 2H), 6.55 (s, 1H), 6.95–7.35 (m, 6H).

1,1-Dioxo-3,3-dibutyl-5-phenyl-7-methylthio-8-carboxymethoxy-2,3,4,5-tetrahydro-1,2,5-benzothiadiazepine Method 5

1,1-Dioxo-3,3-dibutyl-5-phenyl-7-methylthio-8-[N-((R)-α-carboxy-4-hydroxybenzyl) carbamoyl-methoxy]-2,3,4,5tetrahydro-1,2,5-benzothiadiazepine 1,1-Dioxo-3,3-dibutyl-5-phenyl-7-methylthio-8-carboxymethoxy-2,3,4,5-tetrahydro-1,2,5-benzothiadiazepine (Method 3; 295 mg, 0.58 mmol) was dissolved in 10 ml DCM. 4-(1-(R)-t-Butoxycarbonyl-1-aminomethyl)phenol (Method 6; 160 mg, 0.72 mmol), 2,6-lutidine (140 µl, 1.20 mmol) and TBTU (230 mg, 0.72 mmol) were added successively. The mixture was stirred for 3 h. Additional 4-(1-(R)-t-butoxycarbonyl-1-aminomethyl)phenol (Method 6; 10 mg, 0.04 mmol) was added and stirring was continued for 2 h. DCM (20 ml) was added and the solution was washed with 5% NaHCO₃ (20 ml), 0.3M KHSO₄ (20 ml), brine (20 ml) before it was dried and concentrated to a volume of 10 ml. The tert-butyl ester of the title compound was confirmed; m/z: 729 (M+18(NH₄⁺)). TFA (1.3 ml) was added and the mixture was stirred for 4.5 h and concentrated. The crude product was purified by preparative HPLC using a C8 column (5×500 mm) and a gradient (40/60 to 70/30 over 40 min) of MeCN/0.1M ammonium acetate buffer as eluent. Lyophilization yielded the title compound in 77.5% (302 mg). NMR (400 MHz): 0.8 (t, 6H), 1.0–1.2 (m, 6H), 1.25–1.4 (m, 2H) 1.4–1;5 (m, 2H), 1.55–1.7 (m, 2H), 2.1 (s, 3H), 3.95 (brs, 2H), 4.6 (ABq, 2H), 5.3 (s, 1H), 6.6 (s, 1H), 6.75 (d, 2H), 7.05 (t, 1H) 7.15–7.4 (m, 7H); m/z: 673 (M+18 (NH₄⁺)).

Method 6

4-(1-(R)-t-Butoxycarbonyl-1-aminomethyl)phenol

Sulfuric acid (1 ml conc.) was added to a solution of D-(R)-4-hydroxyphenylglycine (1.0 g, 6.0 mmol) in 1,4dioxane (8 ml) placed in a Teflon® flask The flask was cooled to −78° C. and isobutylene (8 g, 142.6 mmol, condensed at −78° C.) was added. The flask was placed in an autoclave at room temperature and stirred for 15 h. The autoclave was cooled on ice before opened. The excess isobutylene was allowed to evaporate and the remaining solution was poured into aqueous NaOH (2M, 20 ml) and was extracted with diethyl ether to remove formed by-product. The aqueous phase was slightly acidified to attain pH=10 using 2M HCl and was extracted with diethyl ether (3×75 ml). The organic phase was washed with brine, dried and concentrated. The obtained product was recrystallized in diethyl etherhexane. Mass: 0.55 g (41%). NMR (600 MHz, CDCl₃): 1.45 (s, 9H), 4.45 (s, 1H), 6.8 (d, 2H), 7.25 (d, 2H); m/z: 224.

What claimed is:

1. A compound of formula (I):

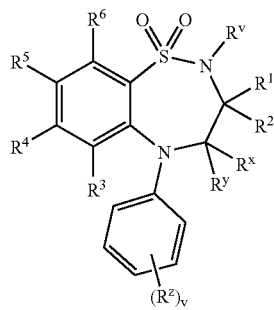

wherein:

$R^v$ is selected from hydrogen or $C_{1-6}$alkyl;

One of $R^1$ and $R^2$ are selected from hydrogen or $C_{1-6}$alkyl and the other is selected from $C_{1-6}$alkyl;

$R^x$ and $R^y$ are independently selected from hydrogen, hydroxy, amino, mercapto, $C_{1-6}$alkyl, $C_{1-6}$alkoxy, N—($C_{1-6}$alkyl)amino, N,N—($C_{1-6}$alkyl)₂amino, $C_{1-6}$alkylS(O)$_a$ wherein a is 0 to 2;

$R^z$ is selected from halo, nitr, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)₂amino, $C_{1-6}$alkanoylamino, N—($C_{1-6}$alkyl)carbamoyl, N,N—($C_{1-6}$alkyl)₂carbamoyl, $C_{1-6}$alkylS(O)$_a$ wherein a is 0 to 2, $C_{1-6}$alkoxycarbonyl, N—($C_{1-6}$alkyl)sulphamoyl and N,N—($C_{1-6}$alkyl)₂sulphamoyl;

v is 0–5;

one of $R^4$ and $R^5$ is a group of formula (IA):

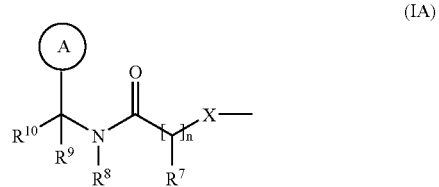

(IA)

$R^3$ and $R^6$ and the other of $R^4$ and $R^5$ are independently selected from hydrogen, halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)₂amino, $C_{1-6}$alkanoylamino, N—($C_{1-6}$alkyl)carbamoyl, N,N—($C_{1-6}$alkyl)₂carbamoyl, $C_{1-6}$alkylS(O)$_a$ wherein a is 0 to 2, $C_{1-6}$alkoxycarbonyl, N—($C_{1-6}$alkyl)sulphamoyl and N,N—($C_{1-6}$alkyl)₂sulphamoyl; wherein $R^3$ and $R^6$ and the other of $R^4$ and $R^5$ may be optionally substituted on carbon by one or more $R^{17}$;

X is —O—, —N($R^a$)—, —S(O)$_b$— or —CH($R^a$)—; wherein $R^a$ is hydrogen or $C_{1-6}$alkyl and b is 0–2;

Ring A is aryl or heteroaryl; wherein Ring A is optionally substituted on carbon by one or more substituents selected from $R^{18}$;

$R^7$ is hydrogen, $C_{1-6}$alkyl, carbocyclyl or heterocyclyl; wherein $R^7$ is optionally substituted on carbon by one or more substituents selected from $R^{19}$; and wherein if said heterocyclyl contains an —NH— group, that nitrogen may be optionally substituted by a group selected from $R^{20}$;

$R^8$ is hydrogen or $C_{1-6}$-alkyl;

$R^9$ is hydrogen or $C_{1-6}$alkyl;

$R^{10}$ is hydrogen, halo, nitro, cyano, hydroxy, amino, carbamoyl, mercapto, sulphamoyl, hydroxyaminocarbonyl, $C_{1-10}$alkyl, $C_{2-10}$alkynyl, $C_{2-10}$alkynyl, $C_{1-10}$alkoxy, $C_{1-10}$alkanoyl, $C_{1-10}$alkanoyloxy, N—($C_{1-10}$alkyl)amino, N,N—($C_{1-10}$alkyl)₂amino, N,N,N—($C_{1-10}$alkyl)₃ammonio, $C_{1-10}$alkanoylamino, N—($C_{1-10}$alkyl)carbamoyl, N,N—($C_{1-10}$alkyl)₂carbamoyl, $C_{1-10}$alkylS(O)$_a$ wherein a is 0 to 2, N—($C_{1-10}$alkyl)sulphamoyl, N,N—($C_{1-10}$alkyl)₂sulphamoyl, N—($C_{1-10}$alkyl)sulphamoylamino, N,N—($C_{1-10}$alkyl)₂sulphamoylamino, $C_{1-10}$alkoxycarbonylamino, carbocyclyl, carbocyclyl$C_{1-10}$alkyl, heterocyclyl, heterocyclyl$C_{1-10}$alkyl, carbocyclyl-($C_{1-10}$alkylene)$_p$-$R^{21}$—($C_{1-10}$alkylene)$_q$- or heterocyclyl-($C_{1-10}$alkylene)$_r$-$R^{22}$—($C_{1-10}$alkylene)$_s$-; wherein $R^{10}$ is optionally substituted on carbon by one or more substituents selected from R$^{23}$; and wherein if said heterocyclyl contains an —NH— group, that nitrogen may be optionally substituted by a group selected from R$^{24}$; or R$^{10}$ is a group of formula (IB):

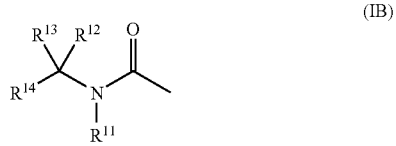
(IB)

wherein:

R$^{11}$ is hydrogen or C$_{1-6}$-alkyl;

R$^{12}$ and R$^{13}$ are independently selected from hydrogen, halo, carbamoyl, sulphamoyl, C$_{1-10}$alkyl, C$_{2-10}$alkenyl, C$_{2-10}$alkynyl, C$_{1-10}$alkanoyl, N—(C$_{1-10}$alkyl)carbamoyl, N,N—(C$_{1-10}$alkyl)$_2$carbamoyl, C$_{1-10}$alkylS(O)$_a$ wherein a is 0 to 2, N—(C$_{1-10}$alkyl)sulphamoyl, N,N—(C$_{1-10}$alkyl)$_2$sulphamoyl, N—(C$_{1-10}$alkyl)sulphamoylamino, N,N—(C$_{1-10}$alkyl)$_2$sulphamoylamino, carbocyclyl or heterocyclyl; wherein R$^{12}$ and R$^{13}$ may be independently optionally substituted on carbon by one or more substituents selected from R$^{25}$; and wherein if said heterocyclyl contains an —NH— group, that nitrogen may be optionally substituted by a group selected from R$^{26}$;

R$^{14}$ is selected from hydrogen, halo, carbamoyl, sulphamoyl, hydroxyaminocarbonyl, C$_{1-10}$alkyl, C$_{2-10}$alkenyl, C$_{2-10}$alkynyl, C$_{1-10}$alkanoyl, N—(C$_{1-10}$alkyl)carbamoyl, N,N—(C$_{1-10}$alkyl)$_2$carbamoyl, C$_{1-10}$alkylS(O)$_a$ wherein a is 0 to 2, N—(C$_{1-10}$alkyl)sulphamoyl, N,N—(C$_{1-10}$alkyl)$_2$sulphamoyl, N—(C$_{1-10}$alkyl)sulphamoylamino, N,N—(C$_{1-10}$alkyl)$_2$sulphamoylamino, carbocyclyl, carbocyclylC$_{1-10}$alkyl, heterocyclyl, heterocyclylC$_{1-10}$alkyl, carbocyclyl-(C$_{1-10}$alkylene)$_p$-R$^{27}$—(C$_{1-10}$alkylene)$_q$- or heterocyclyl-(C$_{1-10}$alkylene)$_r$-R$^{28}$—(C$_{1-10}$alkylene)$_s$-; wherein R$^{14}$ may be optionally substituted on carbon by one or more substituents selected from R$^{29}$; and wherein if said heterocyclyl contains an —NH— group, that nitrogen may be optionally substituted by a group selected from R$^{30}$; or R$^{14}$ is a group of formula (IC):

(IC)

R$^{15}$ is hydrogen or C$_{1-6}$alkyl; and R$^{16}$ is hydrogen or C$_{1-6}$alkyl; wherein R$^{16}$ may be optionally substituted on carbon by one or more groups selected from R$^{31}$;

or R$^{15}$ and R$^{16}$ together with the nitrogen to which they are attached form a heterocyclyl; wherein said heterocyclyl may be optionally substituted on carbon by one or more R$^{37}$; and wherein if said heterocyclyl contains an —NH— group, that nitrogen may be optionally substituted by a group selected from R$^{38}$;

n is 1–3; wherein the values of R$^7$ may be the same or different;

R$^{17}$, R$^{18}$, R$^{19}$, R$^{23}$, R$^{25}$, R$^{29}$, R$^{31}$ and R$^{37}$ are independently selected from halo, nitro, cyano, hydroxy, amino, carbamoyl, mercapto, sulphamoyl, hydroxyaminocarbonyl, C$_{1-10}$alkyl, C$_{2-10}$alkenyl, C$_{2-10}$alkynyl, C$_{1-10}$alkoxy, C$_{1-10}$alkanoyl, C$_{1-10}$alkanoyloxy, N—(C$_{1-10}$alkyl)amino, N,N—(C$_{1-10}$alkyl)$_2$amino, N,N,N—(C$_{1-10}$alkyl)$_3$ammonio, C$_{1-10}$alkanoylamino, N—(C$_{1-10}$alkyl)carbamoyl, N,N—(C$_{1-10}$alkyl)$_2$ carbamoyl, C$_{1-10}$alkylS(O)$_a$ wherein a is 0 to 2, N—(C$_{1-10}$alkyl)sulphamoyl, N,N—(C$_{1-10}$alkyl)$_2$sulphamoyl, N—(C$_{1-10}$alkyl)sulphamoylamino, N,N—(C$_{1-10}$alkyl)$_2$sulphamoylamino, C$_{1-10}$alkoxycarbonylamino, carbocyclyl, carbocyclylC$_{1-10}$alkyl, heterocyclyl, heterocyclylC$_{1-10}$alkyl, carbocyclyl-(C$_{1-10}$ alkylene)$_p$-R$^{32}$—(C$_{1-10}$alkylene)$_q$- or heterocyclyl-(C$_{1-10}$alkylene)$_r$-R$^{33}$—(C$_{1-10}$alkylene)$_s$-; wherein R$^{17}$, R$^{18}$, R$^{19}$, R$^{23}$, R$^{25}$, R$^{29}$, R$^{31}$ and R$^{37}$ may be independently optionally substituted on carbon by one or more R$^{34}$; and wherein if said heterocyclyl contains an —NH— group, that nitrogen may be optionally substituted by a group selected from R$^{35}$;

R$^{21}$, R$^{22}$, R$^{27}$, R$^{28}$, R$^{32}$ or R$^{33}$ are independently selected from —O—, —NR$^{36}$—, —S(O)$_x$—, —NR$^{36}$C(O)NR$^{36}$—, —NR$^{36}$C(S)NR$^{36}$—, —OC(O)N=C—, —NR$^{36}$C(O)— or —C(O)NR$^{36}$—; wherein R$^{36}$ is selected from hydrogen or C$_{1-6}$alkyl, and x is 0–2;

p, q, r and s are independently selected from 0–2;

R$^{34}$ is selected from halo, hydroxy, cyano, carbamoyl, ureido, amino, nitro, carbamoyl, mercapto, sulphamoyl, trifluoromethyl, trifluoromethoxy, methyl, ethyl, methoxy, ethoxy, vinyl, allyl, ethynyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl, N,N-dimethylsulphamoyl, N-methylsulphamoylamino and N,N-dimethylsulphamoylamino;

R$^{20}$, R$^{24}$, R$^{26}$, R$^{30}$, R$^{35}$ and R$^{38}$ are independently selected from C$_{1-6}$alkyl, C$_{1-6}$alkanoyl, C$_{1-6}$alkylsulphonyl, C$_{1-6}$alkoxycarbonyl, carbamoyl, N—(C$_{1-6}$alkyl)carbamoyl, N,N—(C$_{1-6}$alkyl)carbamoyl, benzyl, benzyloxycarbonyl, benzoyl and phenylsulphonyl; and wherein a "heteroaryl" is a totally unsaturated, mono or bicyclic ring containing 3–12 atoms of which at least one atom is chosen from nitrogen, sulphur and oxygen, which heteroaryl may, unless otherwise specified, be carbon or nitrogen linked;

wherein a "heterocyclyl" is a saturated, partially saturated or unsaturated, mono or bicyclic ring containing 3–12 atoms of which at least one atom is chosen from nitrogen, sulphur and oxygen, which heterocyclyl may, unless otherwise specified, be carbon or nitrogen linked, wherein a —CH2- group can optionally be replaced by a —C(O)— group, and a ring sulphur atom may be optionally oxidised to form an S-oxide; and wherein a "carbocyclyl" is a saturated, partially saturated or unsaturated, mono or bicyclic carbon ring that contains 3–12 atoms; wherein a —CH2- group can optionally be replaced by a —C(O) group;

or a pharmaceutically acceptable salt or in vivo hydrolysable ester or amide formed on an available carboxy or hydroxy group thereof.

2. A compound of formula (I) as claimed in claim 1 wherein R$^v$ is hydrogen or a pharmaceutically acceptable salt or in vivo hydrolysable ester or amide formed on an available carboxy or hydroxy group thereof.

3. A compound of formula (I) as claimed in claim 1 wherein $R^1$ and $R^2$ are both butyl or a pharmaceutically acceptable salt or in vivo hydrolysable ester or amide formed on an available carboxy or hydroxy group thereof.

4. A compound of formula (I) as claimed in claim 1 wherein $R^x$ and $R^y$ are both hydrogen or a pharmaceutically acceptable salt or in vivo hydrolysable ester or amide formed on an available carboxy or hydroxy group thereof.

5. A compound of formula (I) as claimed in claim 1 wherein v is 0 or a pharmaceutically acceptable salt or in vivo hydrolysable ester or amide formed on an available carboxy or hydroxy group thereof.

6. A compound of formula (I) as claimed in claim 1 wherein $R^3$ and $R^6$ are both hydrogen or a pharmaceutically acceptable salt or in vivo hydrolysable ester or amide formed on an available carboxy or hydroxy group thereof.

7. A compound of formula (I) as claimed in claim 1 wherein $R^4$ is methylthio or a pharmaceutically acceptable salt or in vivo hydrolysable ester or amide formed on an available carboxy or hydroxy group thereof.

8. A compound of formula (I) as claimed in claim 1 wherein $R^5$ is a group of formula (IA) (as depicted in claim 1) wherein:
X is —O—;
Ring A is aryl; wherein Ring A is optionally substituted on carbon by one or more substituents selected from $R^{18}$;
$R^7$ is hydrogen;
$R^8$ is hydrogen;
$R^9$ is hydrogen;
$R^{10}$ is a group of formula (IB) (as depicted in claim 1):
$R^{11}$ is hydrogen;
$R^{12}$ and $R^{13}$ are independently selected from hydrogen or $C_{1-10}$alkyl;
$R^{14}$ is selected from $C_{1-10}$alkyl carbocyclyl$C_{1-10}$alkyl and heterocyclyl; wherein $R^{14}$ may be optionally substituted on carbon by one or more substituents selected from $R^{29}$; or $R^{14}$ is a group of formula (IC) (as depicted in claim 1);
$R^{15}$ and $R^{16}$ together with the nitrogen to which they are attached form a heterocyclyl; wherein said heterocyclyl may be optionally substituted on carbon by one or more $R^{37}$;
n is 1;
$R^{18}$, $R^{29}$ and $R^{37}$ are independently selected from hydroxy and N—($C_{1-10}$alkyl)carbamoyl; wherein $R^{18}$, $R^{29}$ and $R_{37}$ may be independently optionally substituted on carbon by one or more $R^{34}$; and
$R^{34}$ is carbamoyl.

9. A compound of formula (I) as claimed in claim 1 wherein:
$R^v$ is selected from hydrogen;
$R^1$ and $R^2$ are both butyl;
$R^x$ and $R^y$ are both hydrogen;
v is 0;
$R^3$ and $R^6$ are both hydrogen;
$R^4$ is methylthio; and
$R^5$ is selected from:
N-{(R)-α-[N-2-(S)-3-(R)-4-(R)-5-(R)-2,3,4,5,6-pentahydroxyhexyl)carbamoyl]benzyl}carbamoylmethoxy;
N-{(R)-α-[N-(2-(S)-3-(R)-4-(R)-5-(R)-2,3,4,5,6-pentahydroxyhexyl)carbamoyl]-4-hydroxybenzyl}carbamoylmethoxy;
N-((R/S)-α-{N-[1-(R)-2-(S)-1-hydroxy-1-(3,4-dihydroxyphenyl)prop-2-yl]carbamoyl}4-hydroxybenzyl)carbamoylmethoxy;
N—-[(R)-α-(N-{2-(S)-[N-(carbamoylmethyl)carbamoyl]pyrrolidin-1-ylcarbonylmethyl}carbamoyl)benzyl]carbamoylmethoxy;
N-((R)-α-{N-[2-(3,4,5-trihydroxyphenyl)ethyl]carbamoyl}benzyl)carbamoylmethoxy; and
N-{(R)-α-[N-(2-(R)-3-(S)-4-(S)-5-(R)-3,4,5,6-tetrahydroxytetrahydropyran-2-ylmethyl)carbamoyl]benzyl}carbamoylmethoxy;
or a pharmaceutically acceptable salt or in vivo hydrolysable ester or amide formed on an available carboxy or hydroxy group thereof.

10. A compound of formula (I) selected from:
1,1-Dioxo-3,3-dibutyl-5-phenyl-7-methylthio-8-(N-{(R)-α-[N-(2-(S)-3-(R)-4-(R)-5-(R)-2,3,4,5,6-pentahydroxyhexyl)carbamoyl]benzyl}carbamoylmethoxy)-2,3,4,5-tetrahydro-1,2,5-benzothiadiazepine;
1,1-Dioxo-3,3-dibutyl-5-phenyl-7-methylthio-8-(N-{(R)-α-[N-(2-(S)-3-(R)-4-(R)-5-(R)-2,3,4,5,6-pentahydroxyhexyl)carbamoyl]-4-hydroxybenzyl}carbamoylmethoxy)-2,3,4,5-tetrahydro-1,2,5-benzothiadiazepine;
1,1-Dioxo-3,3-dibutyl-5-phenyl-7-methylthio-8-[N-((R/S)-α-{N-[1-(R)-2-(S)-1-hydroxy-1-(3,4-dihydroxyphenyl)prop-2-yl]carbamoyl}-4-hydroxybenzyl)carbamoylmethoxy]-2,3,4,5-tetrahydro-1,2,5-benzothiadiazepine;
1,1-Dioxo-3,3-dibutyl-5-phenyl-7-methylthio-8-{N-[(R)-α-(N-{2-(S)-[N-(carbamoylmethyl) carbamoyl]pyrrolidin-1-ylcarbonylmethyl}carbamoyl)benzyl]carbamoylmethoxy}-2,3,4,5-tetrahydro-1,2,5-benzothiadiazepine;
1,1-Dioxo-3,3-dibutyl-5-phenyl-7-methylthio-8-[N-((R)-α-{N-[2-(3,4,5-trihydroxyphenyl)ethyl]carbamoyl}benzyl)carbamoylmethoxy]-2,3,4,5-tetrahydro-1,2,5-benzothiadiazepine; and
1,1-Dioxo-3,3-dibutyl-5-phenyl-7-methylthio-8-(N-{(R)-α-[N-(2-(R)-3-(S)-4(S)-5-(R)-3,4,5,6-tetrahydroxytetrahydropyran-2-ylmethyl)carbamoyl]benzyl}carbamoylmethoxy)-2,3,4,5-tetrahydro-1,2,5-benzothiadiazepine;
or a pharmaceutically acceptable salt or in vivo hydrolysable ester or amide formed on an available carboxy or hydroxy group thereof.

11. A process for preparing a compound of formula (I) as claimed in claim 1 or a pharmaceutically acceptable salt thereof which process comprises of:

Process 1): for compounds of formula (I) wherein X is —O—, —NR$^a$ or —S—; reacting a compound of formula (IIa) or (IIb):

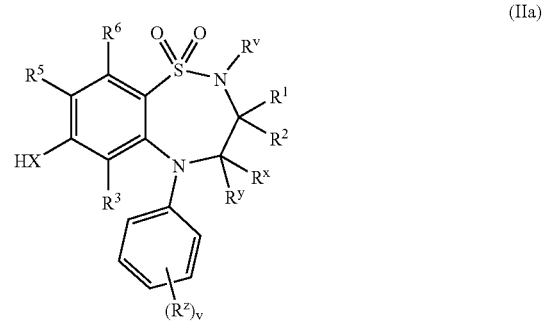

-continued (IIb)

with a compound of formula (III):

(III)

wherein L is a displaceable group;

Process 2): reacting an acid of formula (IVa) or (IVb):

(IVa)

(IVb)

or an activated derivative thereof; with an amine of formula (V):

(V)

Process 3): for compounds of formula (I) wherein $R^{10}$ is a group of formula (IB); reacting a compound of formula (VIa):

(VIa)

or (VIb):

(VIb)

with an amine of formula (VII):

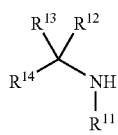
(VII)

Process 4) for compounds of formula (I) wherein one of $R^4$ and $R^5$ are independently selected from $C_{1-6}$alkylthio optionally substituted on carbon by one or more $R^{17}$; reacting a compound of formula (VIIIa) or (VIIIb):

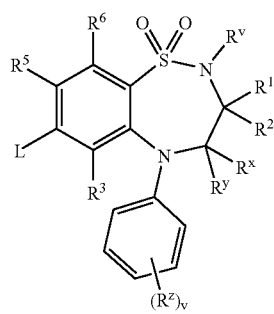
(VIIIa)

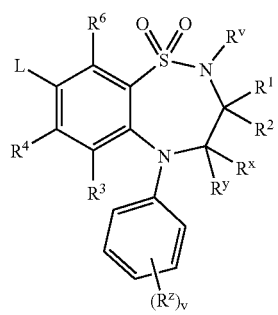
(VIIIb)

wherein L is a displaceable group; with a thiol of formula (IX):

(IX)

wherein $R^m$ is $C_{1-6}$alkylthio optionally substituted on carbon by one or more $R^{17}$; or Process 5): for compounds of formula (I) wherein $R^{14}$ is a group of formula (IC); reacting a compound of formula (Xa):

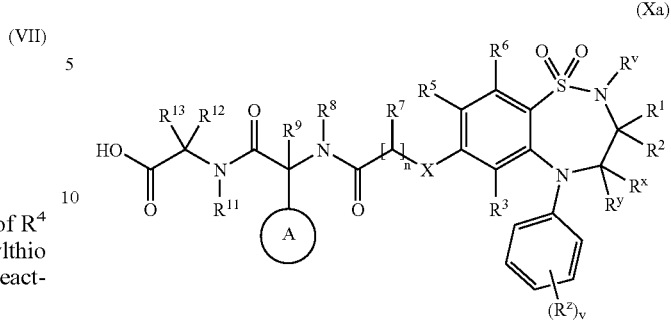
(Xa)

or (Xb):

(Xb)

with an amine of formula (XI):

(XI)

$$R^{16}\!\!-\!\!NH\!-\!R^{15}$$

and thereafter option:
  i) converting a compound of the formula (I) into another compound of the formula (I); and/or
  ii) removing any protecting groups; and/or
  iii) forming a pharmaceutically acceptable salt or in vivo hydrolysable ester or amide formed on an available carboxy or hydroxy group of said compound.

12. A pharmaceutical composition which comprises a compound of formula (I), or a pharmaceutically acceptable salt or in vivo hydrolysable ester or amide formed on an available carboxy or hydroxy group thereof, as claimed in any one of claims 1 to 10, in association with a pharmaceutically-acceptable diluent or carrier.

* * * * *